(12) United States Patent
Gill et al.

(10) Patent No.: US 11,439,795 B2
(45) Date of Patent: Sep. 13, 2022

(54) GUIDEWIRE TORQUE DEVICE AND METHOD OF USE

(71) Applicant: ABBOTT CARDIOVASCULAR SYSTEMS INC., Santa Clara, CA (US)

(72) Inventors: Puneet Kamal Singh Gill, Anaheim, CA (US); Raymundo Rodriguez, Perris, CA (US); Jonathan Durcan, Temecula, CA (US); Robert Hayzelden, Murrieta, CA (US); Michael Green, Pleasanton, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 563 days.

(21) Appl. No.: 16/446,548

(22) Filed: Jun. 19, 2019

(65) Prior Publication Data
US 2020/0398031 A1 Dec. 24, 2020

(51) Int. Cl.
*A61M 25/09* (2006.01)
*A61B 17/00* (2006.01)

(52) U.S. Cl.
CPC ........... *A61M 25/09041* (2013.01); *A61B 2017/0042* (2013.01); *A61M 2025/09116* (2013.01)

(58) Field of Classification Search
CPC .. A61M 25/09041; A61M 2025/09116; A61M 25/0905; A61B 2017/0042
See application file for complete search history.

(56) References Cited

U.S. PATENT DOCUMENTS

| | | | |
|---|---|---|---|
| 1,177,869 A * | 4/1916 | Kelley | B23B 31/103 403/301 |
| 5,951,494 A | 9/1999 | Wang et al. | |
| 6,099,485 A | 8/2000 | Patterson | |
| 6,248,082 B1 | 6/2001 | Jafari | |
| 6,602,208 B2 | 8/2003 | Jafari | |
| 7,144,378 B2 | 12/2006 | Arnott | |
| 7,186,224 B2 | 3/2007 | Windheuser | |
| 7,972,282 B2 | 7/2011 | Clark et al. | |
| 8,403,869 B2 | 3/2013 | Kasasbeh | |
| 8,500,765 B2 | 8/2013 | Shturman | |
| 9,132,536 B2 | 9/2015 | Nino et al. | |
| 9,192,405 B2 | 11/2015 | Shturman | |
| 9,295,815 B2 | 3/2016 | Stevens et al. | |
| 9,352,130 B2 | 5/2016 | Moger | |
| 9,375,553 B2 * | 6/2016 | Chrisman | A61M 25/09041 |
| 9,452,018 B2 | 9/2016 | Yu | |
| 9,770,574 B2 | 9/2017 | McArthur et al. | |
| 9,814,864 B2 | 11/2017 | Scarpine et al. | |
| 2002/0161421 A1 | 10/2002 | Lee et al. | |
| 2007/0219467 A1 | 9/2007 | Clark et al. | |
| 2009/0124934 A1 | 5/2009 | Rabbitte et al. | |
| 2016/0074157 A1 | 3/2016 | Yang et al. | |

OTHER PUBLICATIONS

International Search Report dated Aug. 14, 2020.

* cited by examiner

*Primary Examiner* — David J. McCrosky
(74) *Attorney, Agent, or Firm* — Fulwider Patton LLP

(57) ABSTRACT

A torque device for gripping and manipulating a guidewire for advancing the guidewire into a patient's vascular system. The torque device is configured for single-handed use and can be opened for repositioning the torque device relative to the guidewire and closed for gripping the guidewire to prevent axial and rotational movement relative to the guidewire. The torque device grips the guidewire at multiple spaced apart locations on the guidewire.

24 Claims, 25 Drawing Sheets

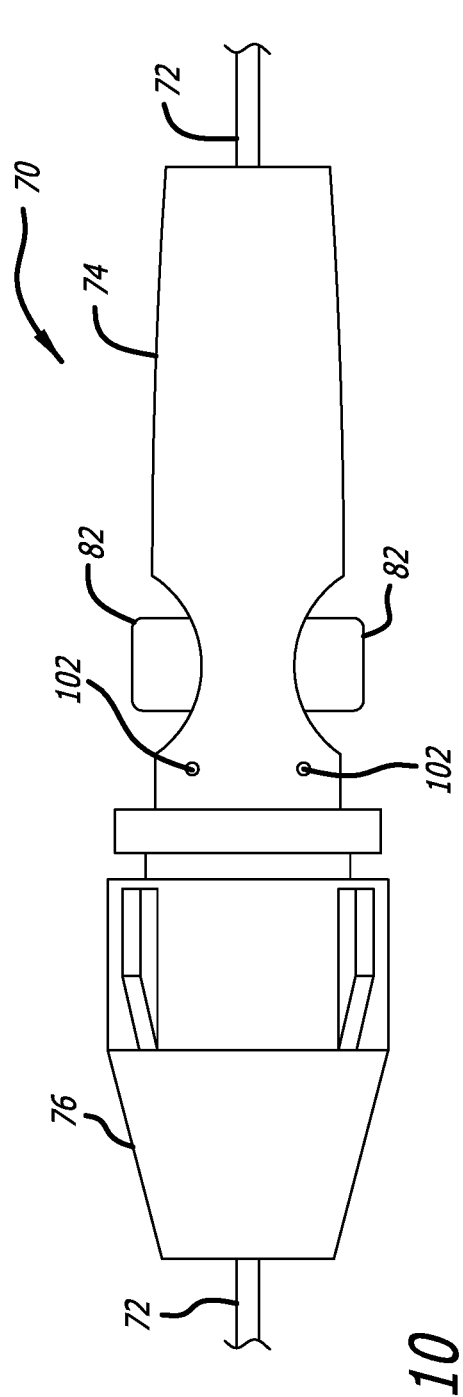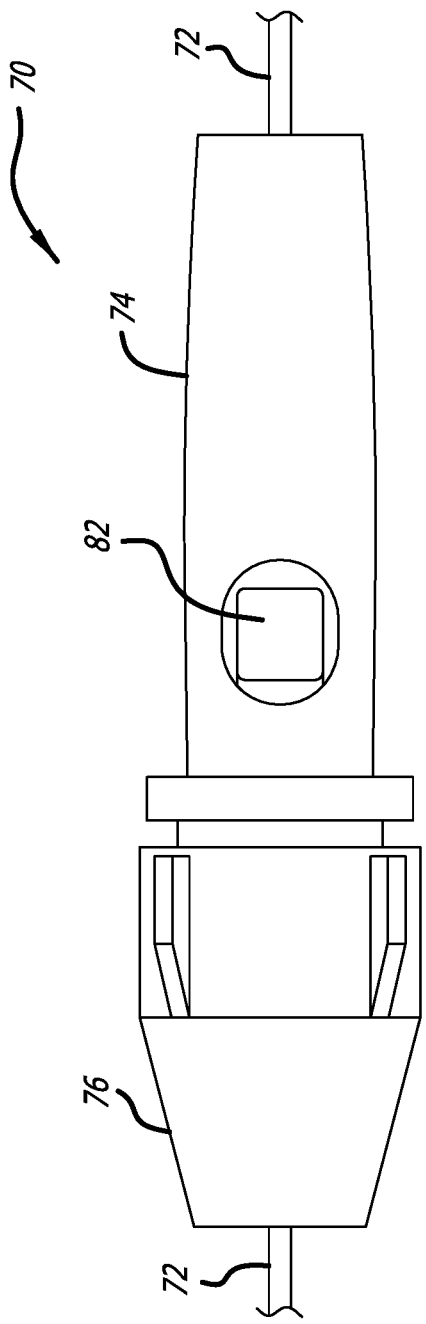

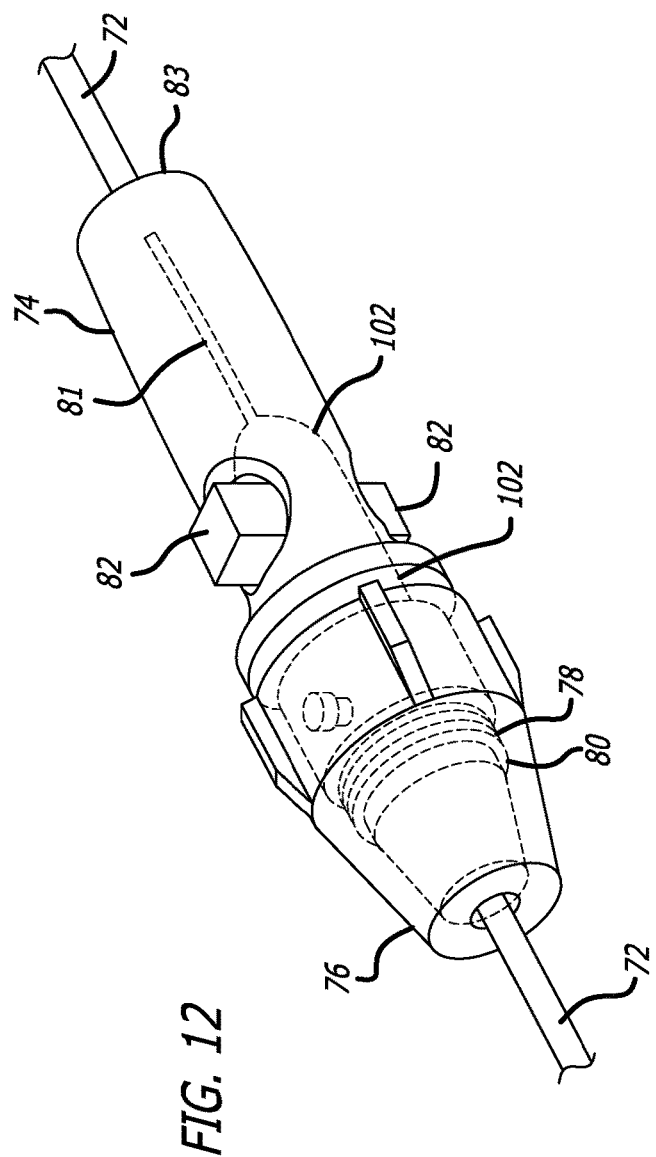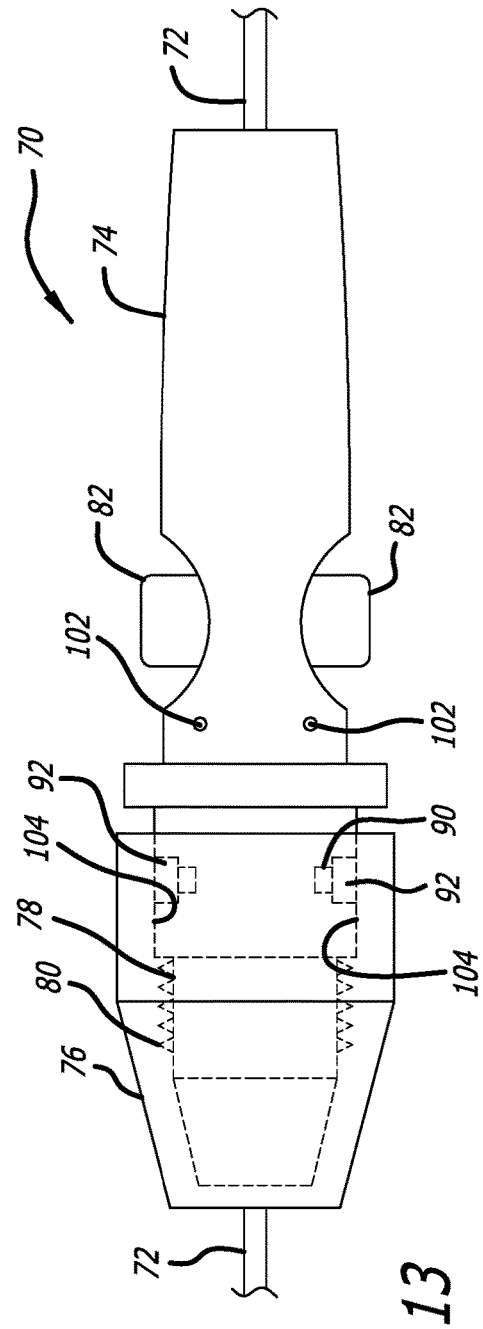

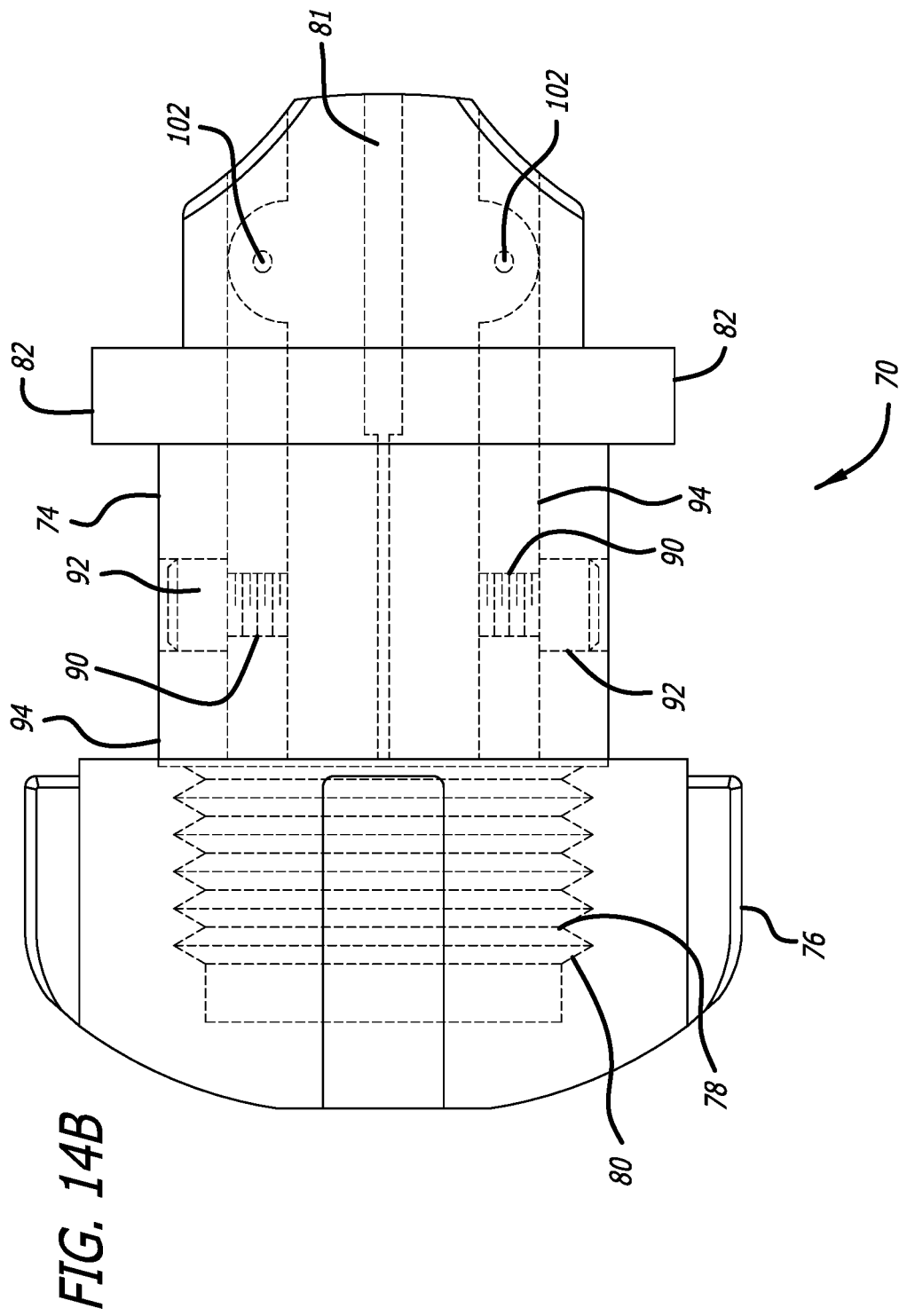

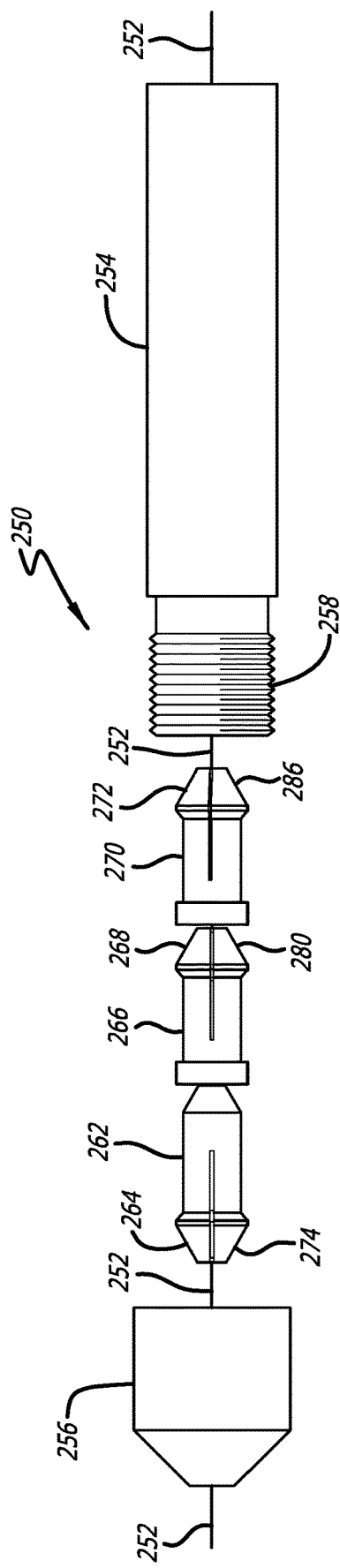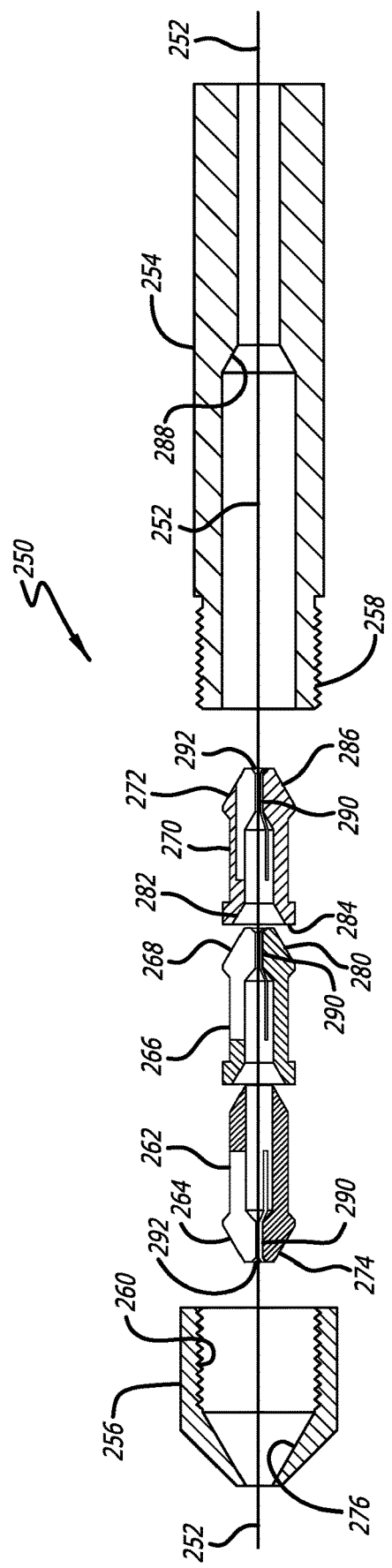

GUIDEWIRE TORQUE DEVICE AND METHOD OF USE

BACKGROUND

Medical guidewires are commonly used for a variety of medical procedures. Such procedures include angioplasty, stenting, pacemaker insertion, electrophysiology studies, atherectomy, and thrombolysis and other coronary and peripheral endovascular procedures, and in endourology and therapeutic endoscopy of the gastrointestinal system. To position a guidewire at a desired location within a patient a medical professional navigates the guidewire through the patient's anatomy by manipulating the guidewire. Such manipulation includes advancing of the guidewire into a patient's vasculature or other portion of the patient's body while torqueing the guidewire. Torqueing the guidewire allows the medical professional to change the spatial orientation of the tip of the guidewire when negotiating tortuous turns and branches in the patient's vasculature such as the coronary arteries, or other relevant portion of the patient's anatomy.

To manipulate the guidewire, medical professionals have traditionally used devices which require two-handed operability. As the guidewire is advanced into the patient's artery, the distance between the patient's body and the torque device decreases. When the proximity between the patient's body and the torque device decreases, the medical professional will loosen the torque device, reposition the torque device proximally along the guidewire to provide an additional length of guidewire between the patient's body and the torque device, and then tighten the torque device to secure its position along the length of the guidewire. The process of loosening and repositioning the torque device may be repeated several times during the placement of the guidewire.

Many of the commercially-available torque devices require two-handed operability to loosen and tighten the device. Due to the complexities of some guidewire placement procedures, it can be inconvenient or impractical for a practitioner to utilize both hands to thread the guidewire through the catheter or reposition the torque device along the length of the guidewire. As a result, additional care and attention are required when manipulating the torque device relative to the guidewire during the procedure. This can lengthen the amount of time and the degree of difficulty necessary to complete the guidewire placement procedure. Additionally, traditional devices are often not adequately intuitive leading to misuse of the device and inadvertent damage to the guidewire. These devices can require specialized training to facilitate proper usage of the device and can still result in inadvertent misuse of the device during the course of the procedure. Additionally, some devices do not provide adequate gripping of the guidewire as may be required to push the guidewire through a calcified vascular lesion or other guidewire path occlusion. Where an occlusion is encountered, the practitioner may over tighten the device in a manner that causes damage to the guidewire such as kinking the wire or damaging a coating on the wire.

Generally, guidewires have a lubriquous or hydrophilic coating on the distal portion of the wire and a hydrophobic coating (PTFE) on the proximal portion of the wire to provide lubricity to permit the guidewire to pass more easily through a blood vessel. However, due to the lubricity, sufficient torque cannot be applied by simply rolling or twisting the proximal end of the guidewire by the clinician. Consequently, a torque apparatus is needed to grip the guidewire having a hydrophilic coating for adequate torque application without damaging the coating. When the clinician needs to reposition the torque apparatus along the guidewire, the user grasps one end of the torque apparatus while actuating a mechanism to release the guidewire with the other hand. The torque apparatus is then moved along the guidewire to reposition the torque device along the guidewire. As a result of the two-handed operation required to release the guidewire and reposition the torque apparatus, another clinician is needed to hold the guidewire steady while the torque device is repositioned, all the while being careful to not damage the coatings on the guidewire. Additionally, when repositioning the torque device the physician releases the guidewire while trying to position the torque device, which can easily result in losing the wire position in the patient or even slide out and get contaminated.

Physicians and patients would benefit from a single-handed torque device that would allow the physician to quickly reposition the torque device with one hand thereby saving time and reducing the potential for risk to the patient.

SUMMARY OF THE INVENTION

Multiple embodiments are disclosed herein relating to a guidewire torque device which allows the physician to use the torque device with one hand, or provides multiple gripping locations along the guidewire. The torque devices disclosed herein are used for gripping or securing and releasing a guidewire to permit rotational and longitudinal manipulation of the guidewire to steer the guidewire through a vessel or other tortuous anatomy. In some embodiments disclosed herein, the torque device is configured for single handed operation by the physician. In other embodiments, the torque device provides multiple spaced apart gripping locations so that the gripping force is increased relative to a single gripping location along the guidewire.

BRIEF DESCRIPTION OF THE DRAWINGS

FIG. 10. is a side view of the torque device of FIG. 9.

FIG. 11 is a top view of the torque device of FIG. 9.

FIG. 12 is a perspective view, partially in section, of the torque device of FIG. 9.

FIG. 13 is a side, partial cross-sectional view, of the torque device of FIG. 9.

FIG. 14B is a cross-sectional, side view, of the torque device of FIG. 9.

FIG. 25 is an exploded side view of a torque device for use in gripping and manipulating a guidewire having three spaced apart gripping locations.

FIG. 26 is a side, cross-sectional view, of the torque device of FIG. 25.

DETAILED DESCRIPTION OF THE PREFERRED EMBODIMENTS

Figure 1:
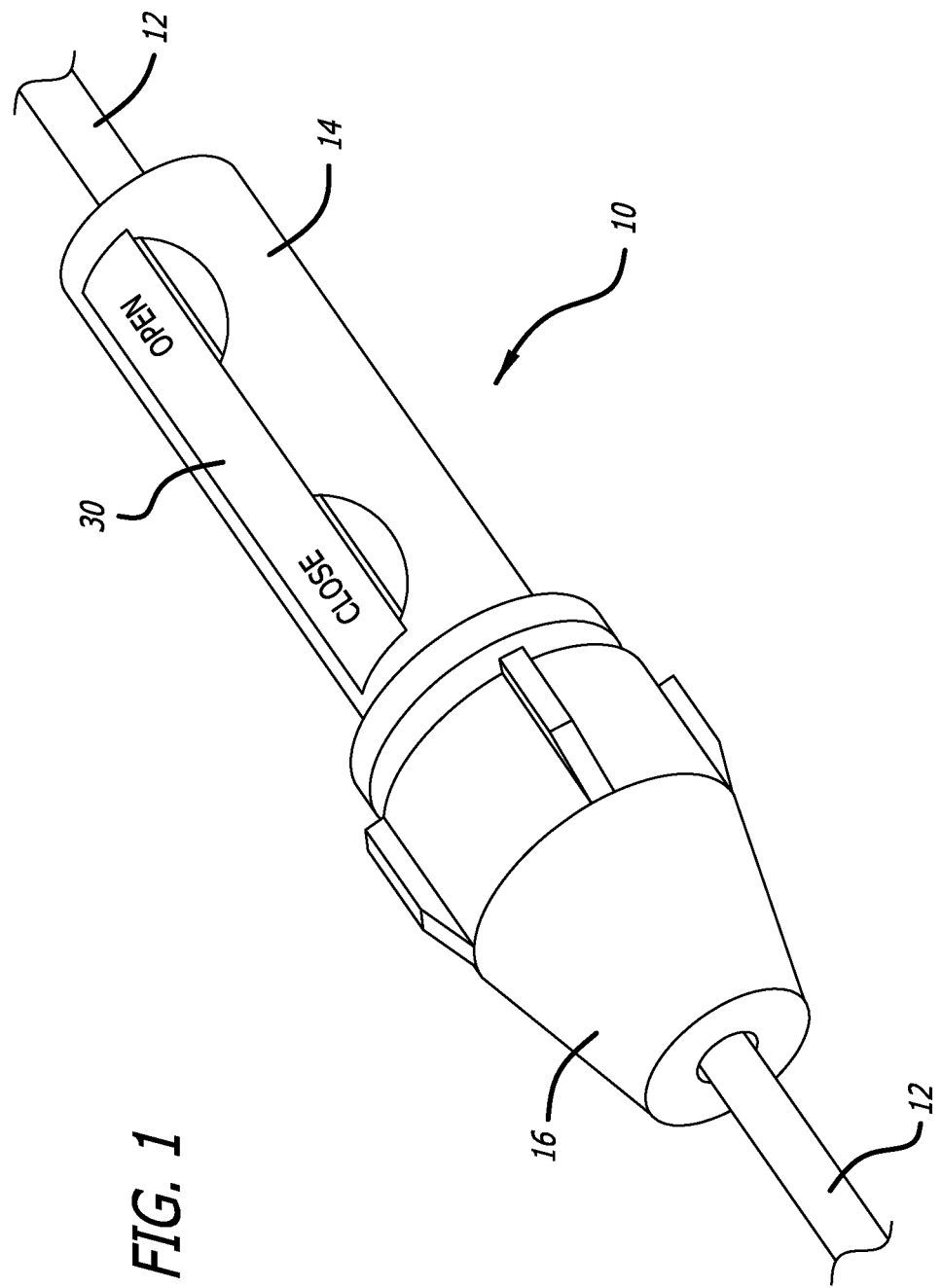
FIG. 1 is a perspective view of a torque device for use in gripping and manipulating a guidewire.
Figure 2:
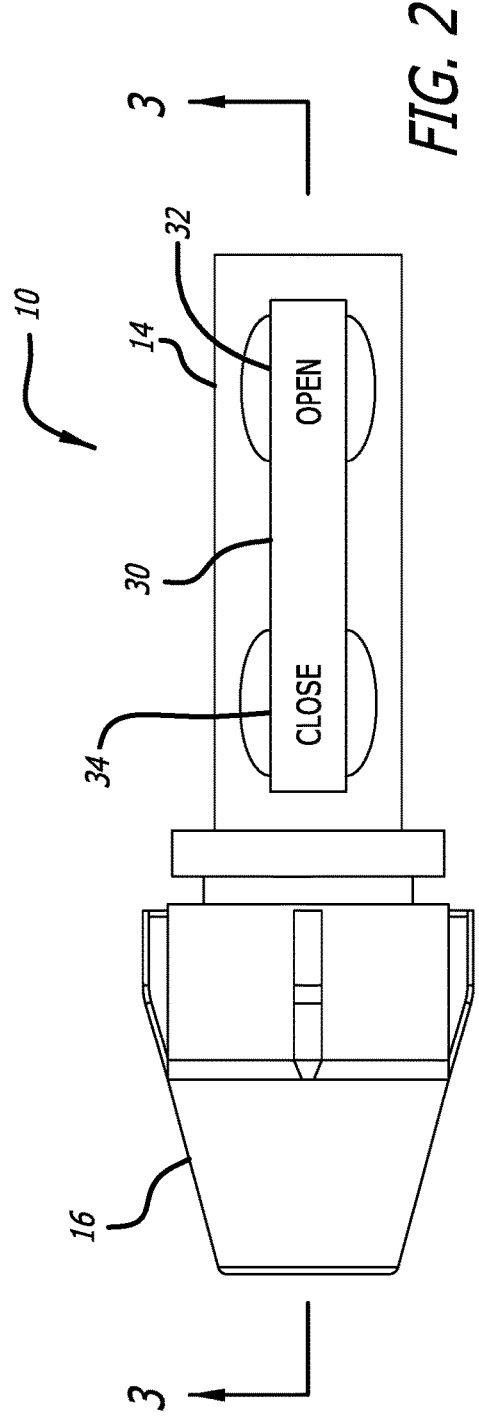
FIG. 2 is a top view of the torque device of FIG. 1.
Figure 3:
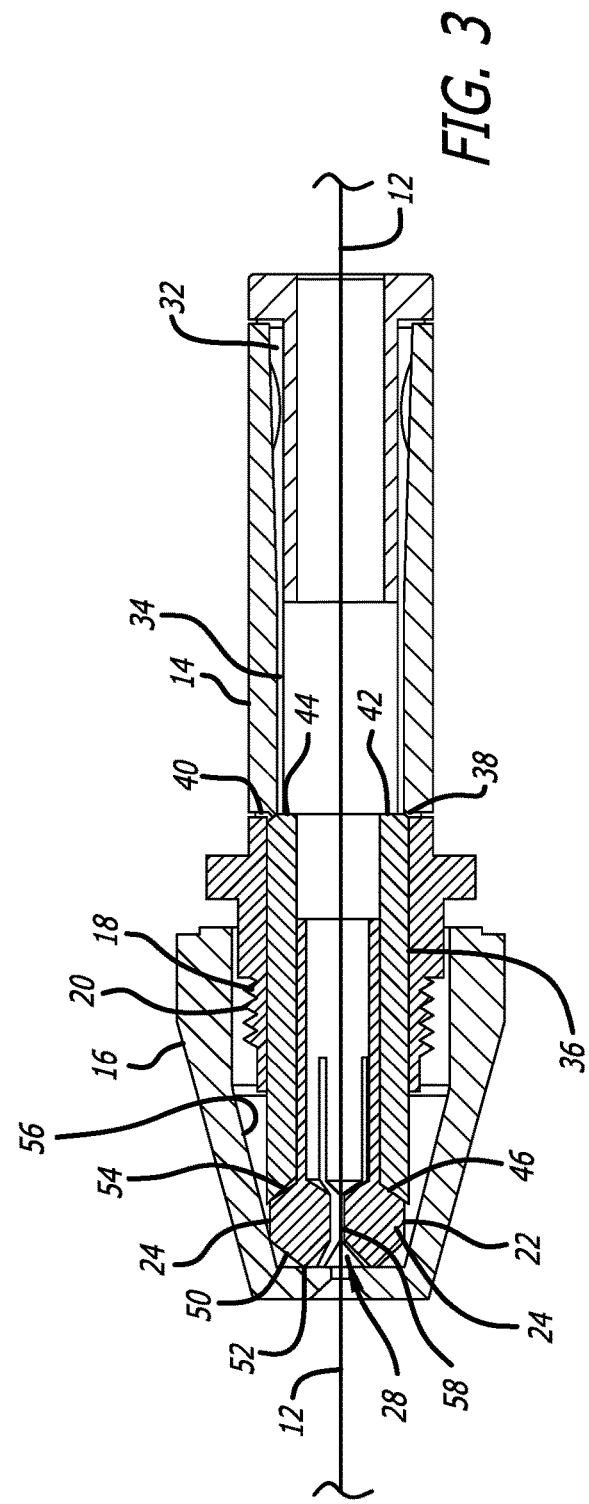
FIG. 3 is a longitudinal cross-sectional side view of the torque device of FIG. 2 taken along the lines 3-3.
Figure 4:
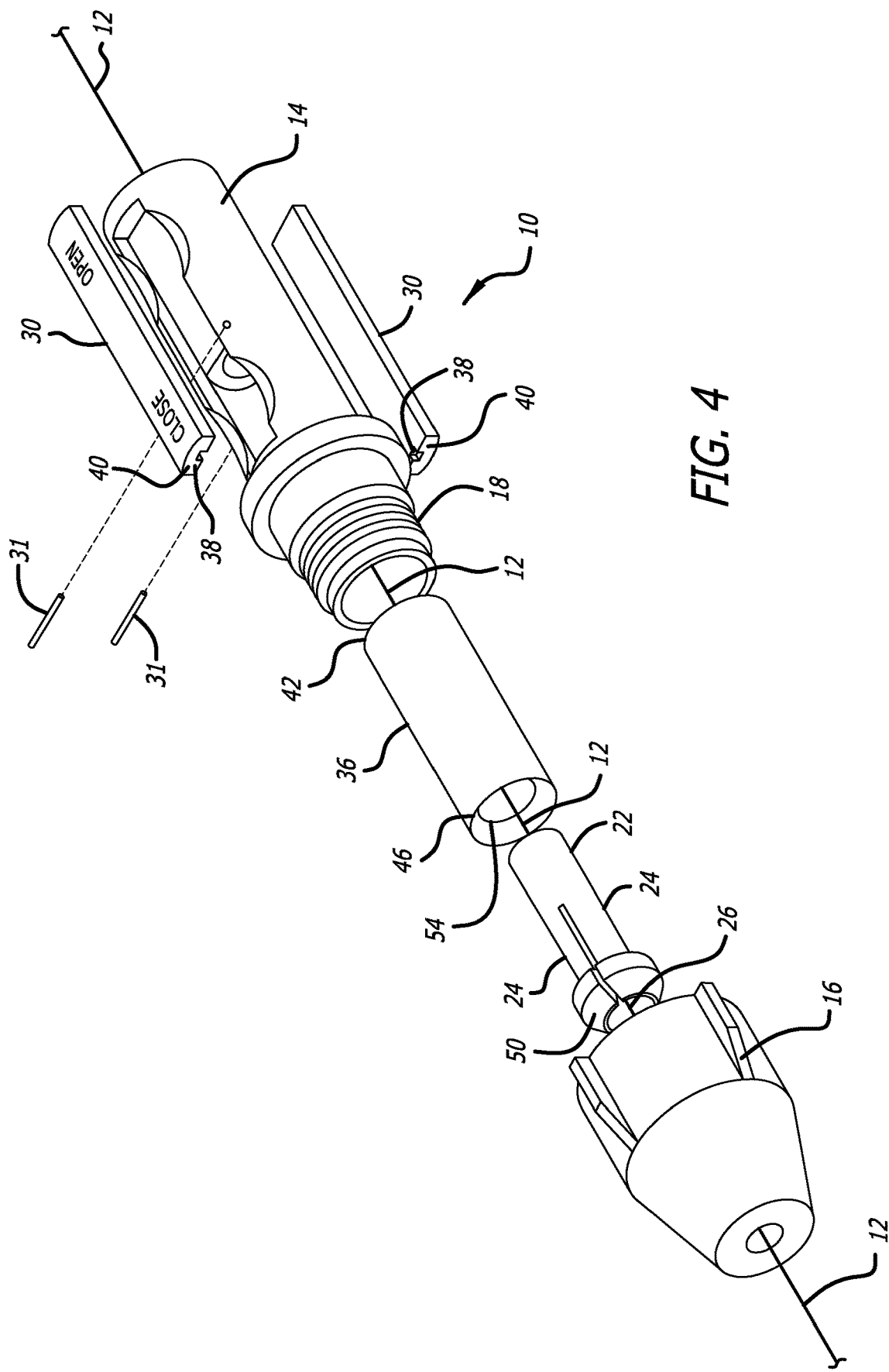
FIG. 4 is an exploded perspective view of the torque device of FIG. 1 depicting the cap, collet, sleeve, body and control levers.
Figure 5:
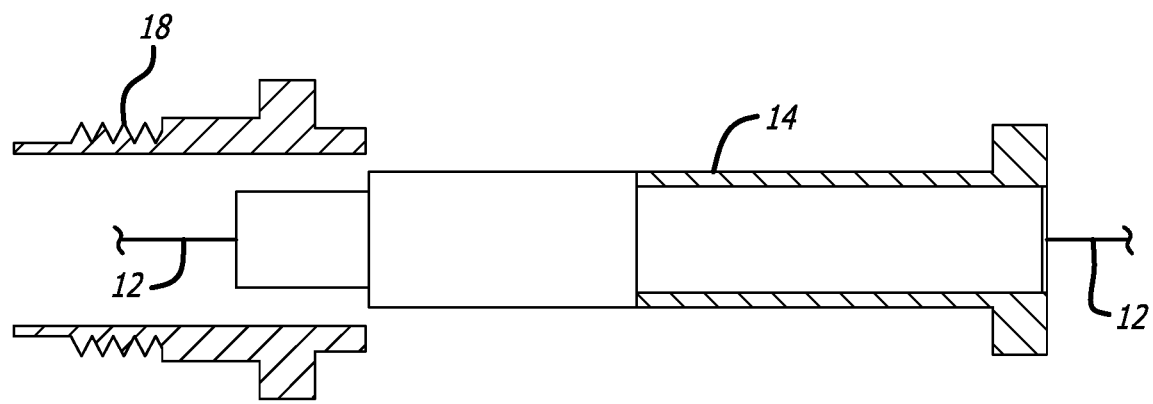
FIG. 5 is an exploded cross-sectional view of the body portion of the torque device of FIG. 1.
Figure 6:
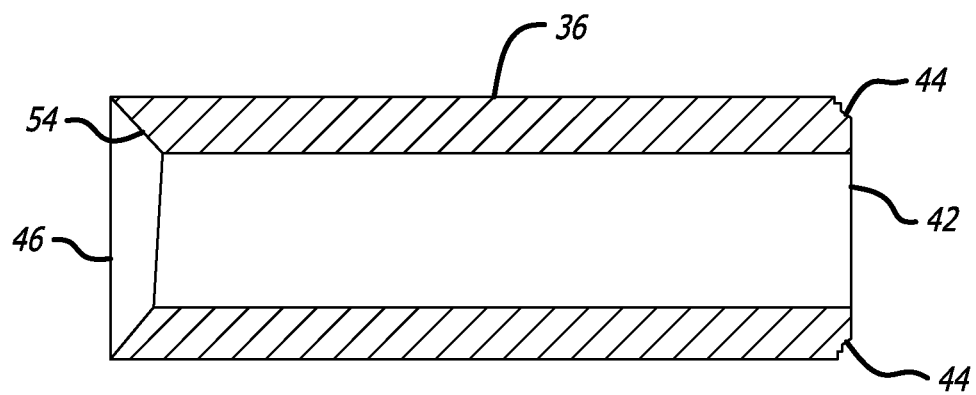
FIG. 6 is a cross-sectional view of the sleeve of the torque device of FIG. 1.
Figure 7A:
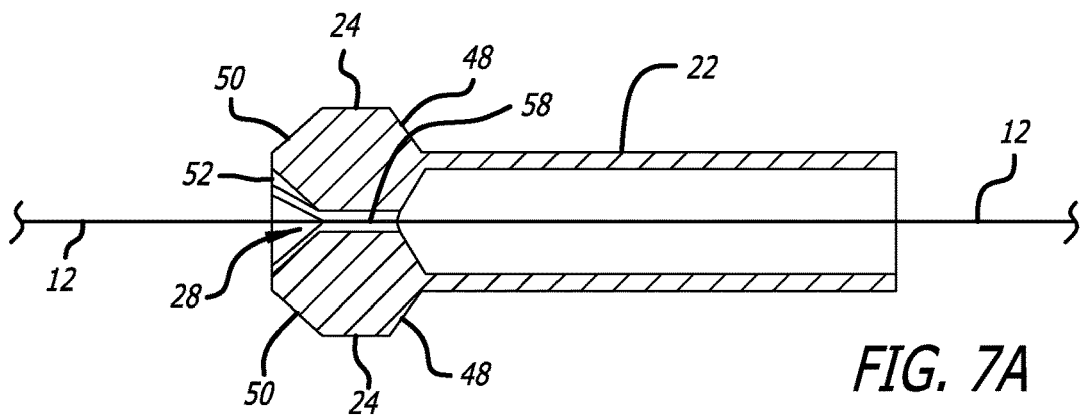
FIG. 7A is a cross-sectional view of the collet of the torque device of FIG. 1 in a closed configuration.
Figure 7B:
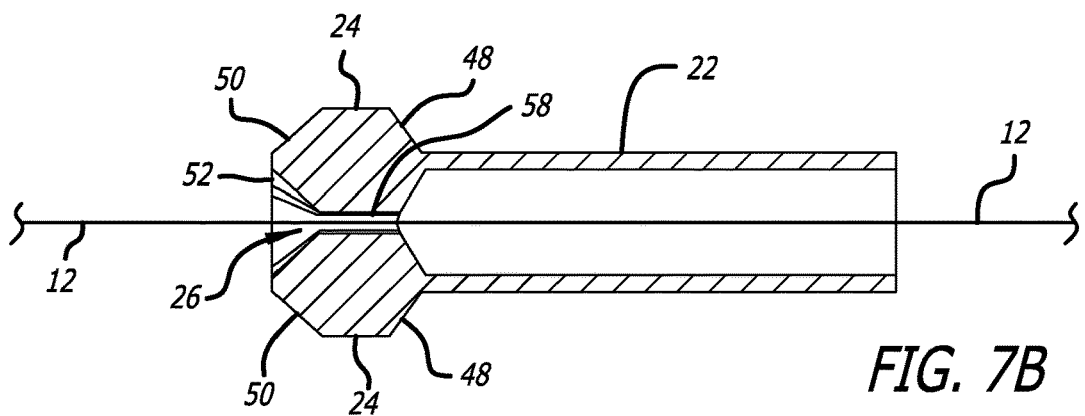
FIG. 7B is a cross-sectional view of the collet of the torque device of FIG. 1 in an open configuration
Figure 8:
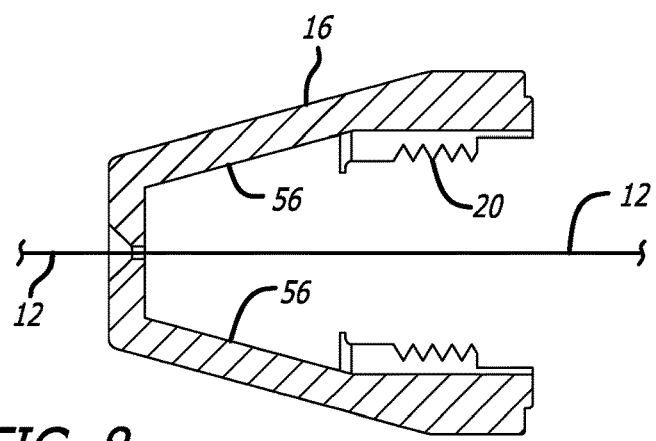
FIG. 8 is a cross-sectional view of the cap of the torque device of FIG. 1.
Figure 9:
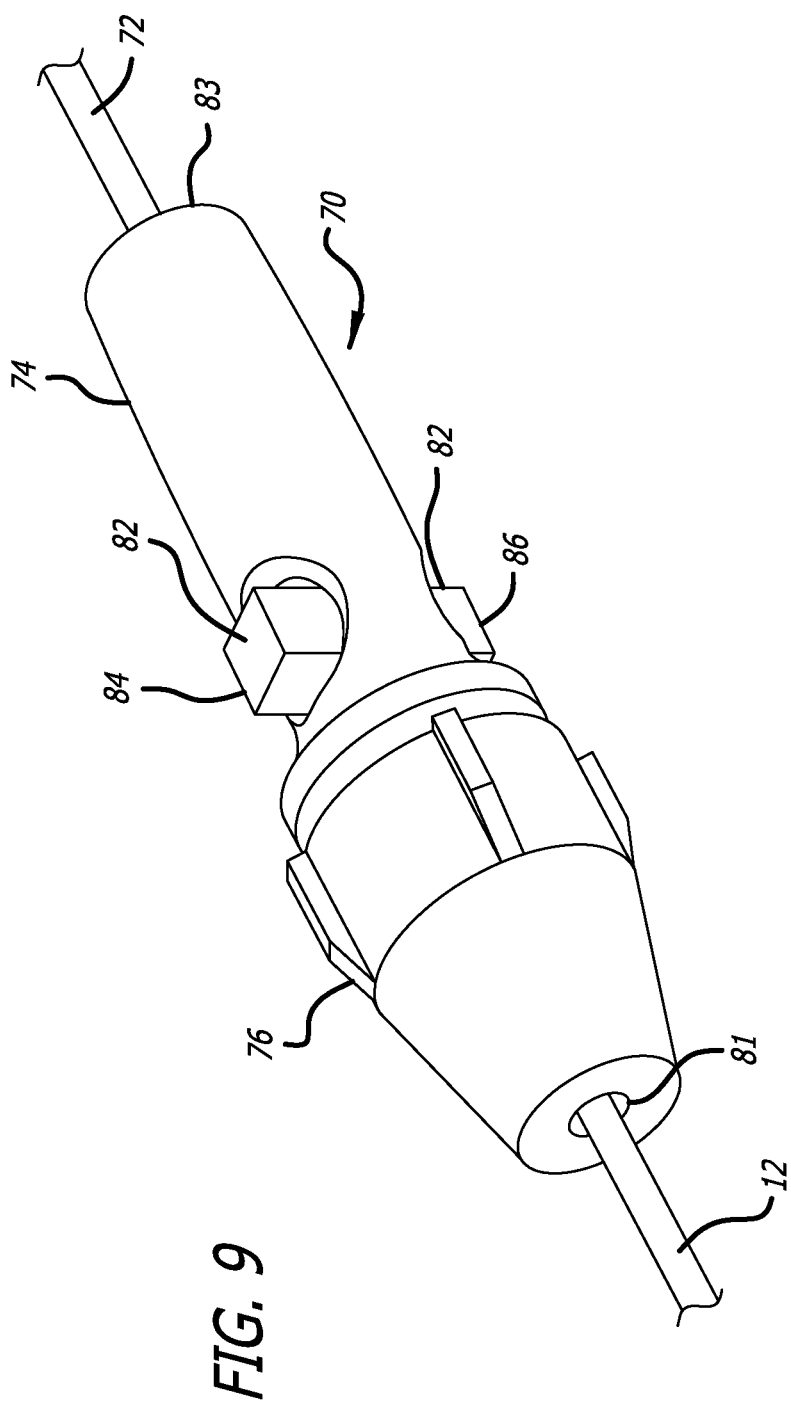
FIG. 9 is a perspective view of a torque device for use in gripping and manipulating a guidewire.
Figure 14A:
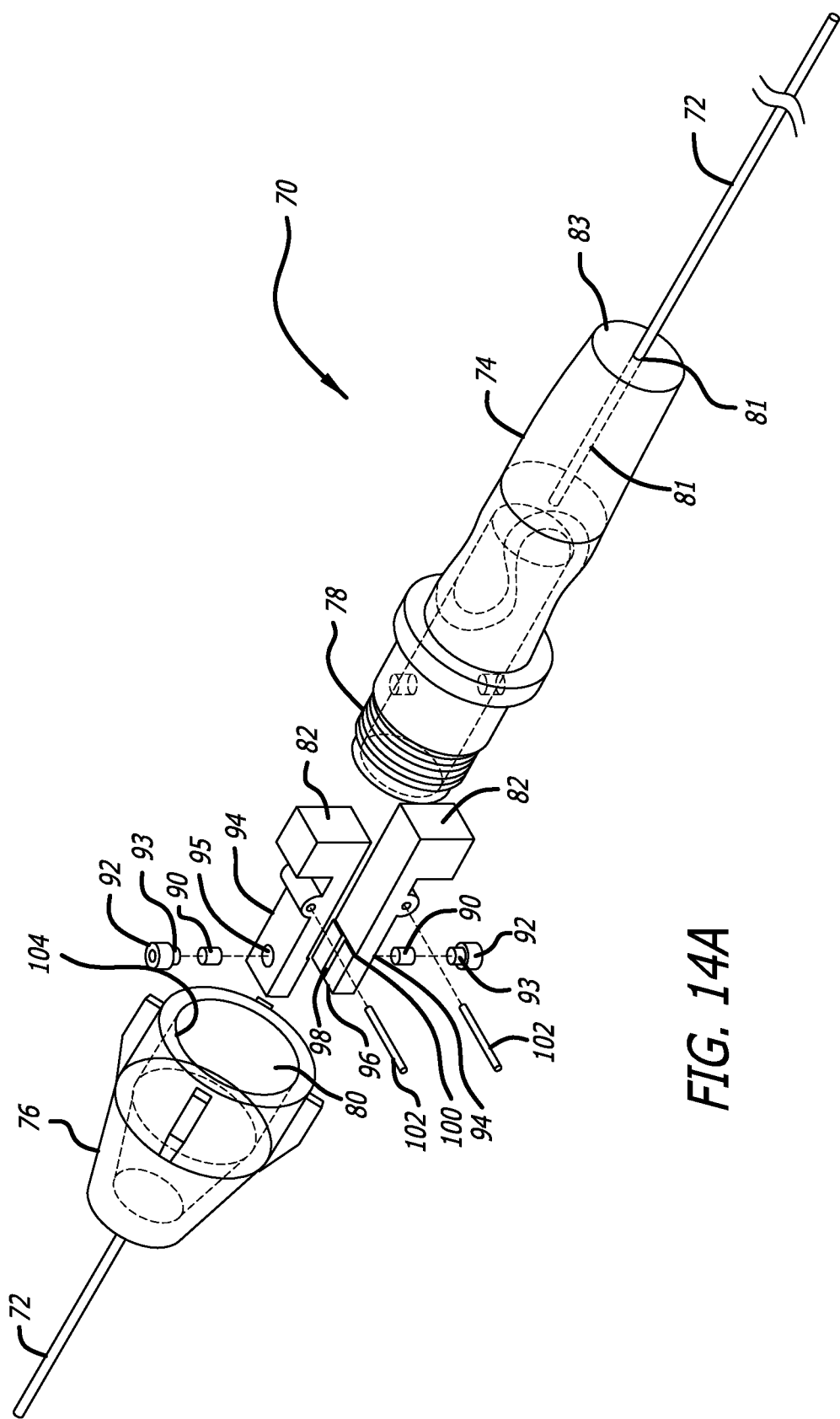
FIG. 14A is an exploded perspective view, partially in section, of the torque device of FIG. 9.

Embodiments disclosed herein relate to a medical guidewire torque device which offers advantages which are not currently available in prior art devices. The torque devices disclosed herein are used for attaching to and selectively gripping or securing and releasing a guidewire to permit rotational and longitudinal manipulation of the guidewire to steer the guidewire through a vessel or series of vessels or other tortuous anatomy. The torque device provides an advantage to the physician in manipulating the guidewire in tortuous anatomy.

In one embodiment, as shown in FIGS. 1-8, a torque device 10 is used to grip, manipulate, and release a guidewire 12, and reposition the torque device using single handed operation. The torque device 10 includes a body 14 and a cap 16. The body 14 has body threads 18 and cap 16 has cap threads 20 so that the cap can be screwed onto the body. A collet 22 is enclosed in the body 14 and is retained inside the body after the cap 16 is screwed onto the body threads 18. The collet 22 has a plurality of longitudinally extending fingers 24 that are spring biased towards an open position 26. When the fingers are in a compressed and closed position 28, the fingers will grip the guidewire 12 and securely retain it for manipulation and advancing into the vascular system. The body also includes a control lever 30 that is pivotally mounted by pins 31 on the body and has an open position 32 and a closed position 34. A sleeve 36 also is retained inside the body 14 and the sleeve overlaps at least a portion of the collet 22. The collet 22 and the sleeve 36 can slide relative to each other in a longitudinal direction. When the control lever 30 is moved to the closed position 34, a cam 38 on the distal end 40 of the control lever moves into engagement with a proximal end 42 of the tubular sleeve 36 thereby moving the tubular sleeve distally toward the cap 16. The tubular sleeve 36 has a cam surface 44 on its proximal end 42 which engages the cam 38 as the control lever is moved from the open position 26 to the closed position 28. As the tubular sleeve 36 moves distally, a distal end 46 of the tubular sleeve 36 engages the collet 22. The collet has a first tapered face 48 and a second tapered face 50 at the collet distal end 52. The tubular sleeve 36 has a tapered distal end 54 that slides on the first tapered face 48 of the collet 22, thereby forcing the collet to move distally. As the collet moves distally, the second tapered face 50 of the collet engages a tapered surface 56 on the cap as the collet continues to move distally. As the collet 22 continues to move distally, the second tapered face 50 engages and slides along the tapered surface 56 of the cap 16 which in turn compresses the plurality of fingers 24 onto the guidewire, thereby gripping the guidewire 12 so that the torque device can move the guidewire without sliding along the longitudinal surface of the guidewire. As the collet 22 slides distally toward the cap, a force vector is generated by the second tapered face 50 of the collet sliding along the tapered surface 56 of the cap. The force vector overcomes the spring bias of the plurality of fingers, which are spring biased toward the open position. A gripping surface 58 on the collet 22 is forced onto the guidewire to securely grip the guidewire so that the torque device 10 can then be used by the physician to manipulate the guidewire. When the control lever 30 is depressed toward the open position 26, the cam 38 on the distal end of the control lever moves to disengage with the cam surface 44 on the tubular sleeve. After cam 38 disengages from the cam surface 44, the plurality of fingers 24 on the collet 22 spring apart to the open position thereby moving the collet and the tubular sleeve 36 proximally to cause the gripping surface 58 on the collet to release the guidewire. As the plurality of fingers 24 continue to move toward the open position, the second tapered surface 50 of the collet slides proximally on the tapered surface 56 of the cap thereby continuing to release the plurality of fingers to spring apart to the open position.

In another embodiment, as shown in FIGS. 9-14B, a torque device 70 is used to grip, manipulate and release a guidewire 72, and reposition the torque device using single handed operation. The torque device 70 includes a body 74 and a cap 76. The body 74 has body threads 78 and the cap 76 has cap threads 80 so that the cap can be screwed onto the body. A button 82 is positioned inside the body with a portion of the button extending out of the body about midway along the length of the body. The button 82 can be positioned anywhere along the body including at the proximal end 83 where the guidewire 72 enters the body. A guidewire lumen 81 extends through the body and the cap and the guidewire can be gripped, manipulated and released as necessary during a medical procedure. The button 82 has an open position 84 and a closed position 86, wherein the open position allows the guidewire to move freely through the guidewire lumen 81, and in the closed position 86, the guidewire is firmly gripped so that it cannot move longitudinally or rotationally relative to the torque device 70. The button 82 further comprises a pair of clamping jaws 94. Each clamping jaw 94 has a recess 95 configured to receive a spring 90 into the recess. A setscrew 92 screws into the body 74 and has a flat extended nub 93 that has a diameter that is smaller than an inner diameter of spring 90. The recess 95 has a diameter slightly larger than the diameter of spring 90, thus the nub 93 extends into the spring 90 and holds it in place in the recess 95. These two structures, the nub 93 and the recess 95 securely hold the spring 90 in place. The spring 90 exerts a spring force on the clamping jaws 94 toward the closed position 86. The setscrews 92 have threads for engaging threads on the body. The clamping jaws 94 each have a clamp surface 96 which contains V-shaped grooves 98. The V-shaped grooves are configured to receive the guidewire 72 so that when the clamp surfaces 96 are compressed together, the V-shaped grooves will cradle the guidewire 72 and apply significant gripping force so that the guidewire will not move longitudinally or rotationally relative to the torque device 70. The V-shaped grooves can have other configurations such as a U-shaped groove, and may be textured to provide higher gripping force. The clamp surface 96 and V-shaped grooves 98 can be made out of a metallic material, such as brass, which will provide substantial clamping force onto the guidewire 72 without damaging the guidewire or any coating material on the guidewire. The clamp surface 96 and V-shaped grooves 98 are on a raised ledge 100, as can be seen in FIG. 14A, so that other surfaces of the clamping jaws 94 and the button 82 do not contact the guidewire when the button is in the closed position 86. Depressing the button 82 to the open or closed positions is accomplished by the button 82 pivoting on receiving pins 102, which extend through button 82 and are mounted to the body 74 so that the button can pivot back and forth as the open and closed button is depressed. In operation, the torque device 70 is designed so that the springs 90 bias the clamping jaws 94 toward the closed position 86. In this configuration, the springs 90 are compressed, and provide sufficient force to push the clamping jaws 94 closed so that the clamp surfaces 96 provide good clamping force on the guidewire 72, which cannot move longitudinally or rotationally relative to the body 74. In this position, the closed position 86 on the button 82 is engaged. To be clear, the torque device 70 is spring biased to the closed position 86 by the springs 90 exerting a radially outward force against recess 95 in the clamping jaws 94, which in turn moves the clamping jaws together. When the physician wants to reposition the torque device 70 relative to the guidewire 72, the button 82 is depressed to the open position 84 and the clamping jaws 94 move apart as the button 82 pivots on the pivot pins 102 and overcome the force of the springs 90, i.e., the springs 90 elongate slightly allowing the clamping jaws 94 to move apart and release the guidewire 72. The torque device 70 can then be repositioned axially along the guidewire 72. The button 82 is then depressed toward the closed position 86, wherein the springs 90 expand radially outwardly pushing the clamping jaws 94 to move toward each other so that the V-shaped grooves 98 in the clamp surfaces 96 again engage the guidewire 72. It is important to emphasize that all the foregoing operations of the torque device 70 are accomplished by the physician using only one hand on the device, thereby freeing the other hand to maintain the position of the guidewire relative to the patient.

In an alternative embodiment shown in FIGS. 9-14B, one collet may slide within the other and mate with a shoulder to enable both collet ends to be compressed when screwing the cap closed. This may also be achieved by this contacting end having a shoulder on both collets providing a centering feature within the body and provide a backing for compression of the fingers.

Figure 15:
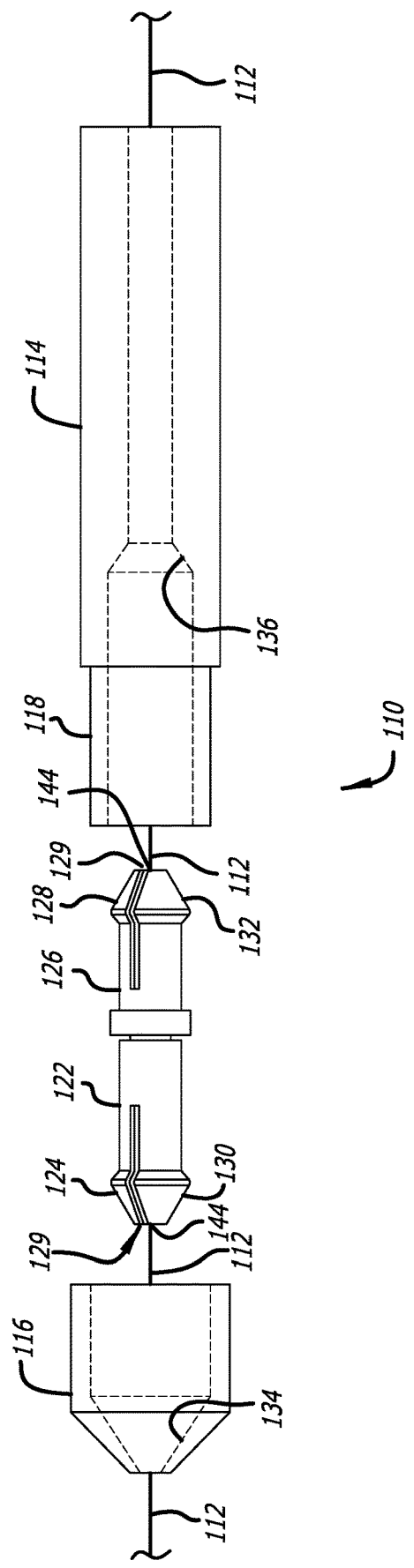
FIG. 15 is an exploded side view of a torque device for use in gripping and manipulating a guidewire having two spaced apart gripping locations.
Figure 16A:
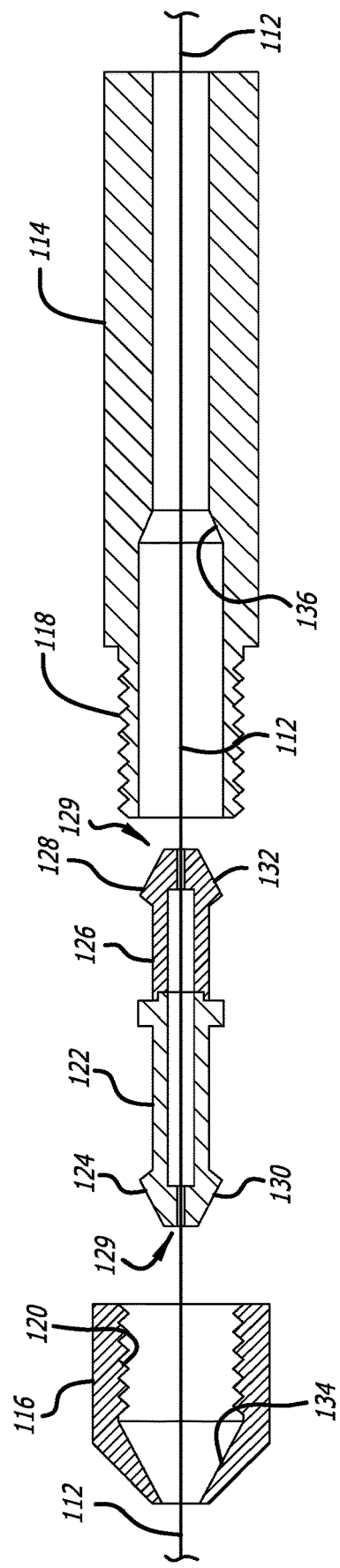
FIG. 16A is a side, cross-sectional view, of the torque device of FIG. 15.
Figure 16B:
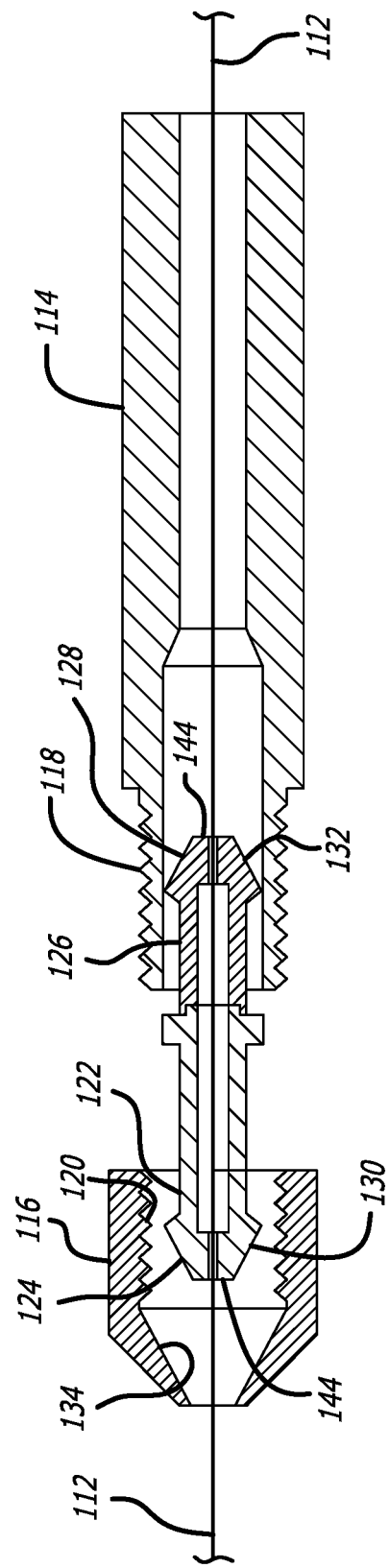
FIG. 16B is a side, cross-sectional view, of the torque device of FIG. 15.
Figure 16C:
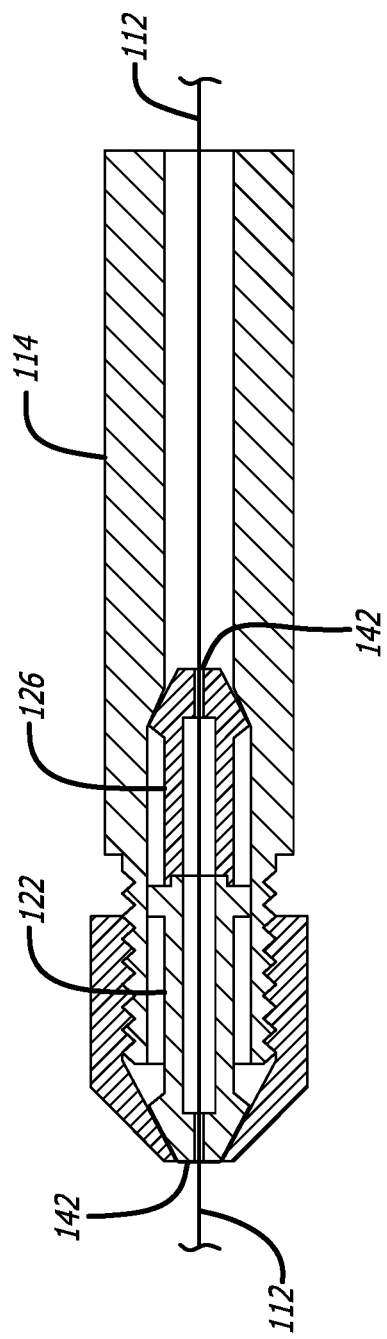
FIG. 16C is a side, cross-sectional view, of the torque device of FIG. 15.

In another embodiment, as shown in FIGS. 15-16C, a torque device 110 is used to grip, manipulate and release a guidewire 112 using two hands to operate the device. Importantly, in this embodiment, the torque device applies gripping force on the guidewire at two separate locations, thereby doubling the gripping force which allows the physician to more easily manipulate and advance the guidewire. The torque device 110 includes a body 114 and a cap 116. The body 114 has body threads 118 and the cap 116 has cap threads 120 so that the cap can be screwed onto the body. A first collet 122 is connected or attached to a second collet 126. The first collet has a first fingers 124 and the second collet 126 has second fingers 128, the first fingers 124 pointing in a direction opposite to that of the second fingers 128. The first collet 122 and the second collet 126 are enclosed in the cap 116 and the body 114 when the cap is screwed onto the body. In order for the first collet 122 and the second collet 126 to apply gripping force on the guidewire 112, the cap 116 is screwed onto the body 114 thereby enclosing the first collet 122 and the second collet 126 inside the cap and the body. A tapered surface 130 on the first collet engages a tapered surface 134 on the cap thereby forcing the first fingers 124 towards a compressed position 142. Similarly, as the cap 116 continues to screw onto the body portion 114, a tapered surface 132 on the second collet engages a tapered surface 136 on the body thereby compressing the second fingers 128 into the compressed position 142. Each of the first fingers 124 and the second fingers 128 has a gripping surface 129 that directly contacts the guidewire 112 when the fingers are in the compressed position 142. Importantly, the compressed position 142 between the first fingers 124 and the second fingers 128 are spaced apart thereby providing two points of contact or gripping force on the guidewire thereby doubling the gripping force without damaging the guidewire or any coating thereon. The first collet 122 and the second collet 126 are formed from any metal or polymer that will not damage the guidewire, and preferably are made from brass. By unscrewing the cap from the body, the fingers will open to an open position 144 since the fingers are spring biased toward an open position. In other words, as cap 116 is unscrewed from the body 114, the tapered surface 130 of the first collet moves away from the tapered surface 134 of the cap, thereby allowing the first fingers to spring outwardly away from each other since they are spring biased open. This moves the first fingers 124 toward the open position 144. Likewise, as the cap 116 is unscrewed from the body 114, the tapered surface 132 on the second collet 126 slides away from the tapered surface 136 of the body 114 allowing the second fingers 128 to spring radially outwardly open toward the open position 144. In the open position 144, the torque device can be moved axially along the guidewire 112 so that it can be repositioned and then the cap 116 again screwed onto the body 114 to move both sets of fingers to the compressed position 142.

Figure 17A:
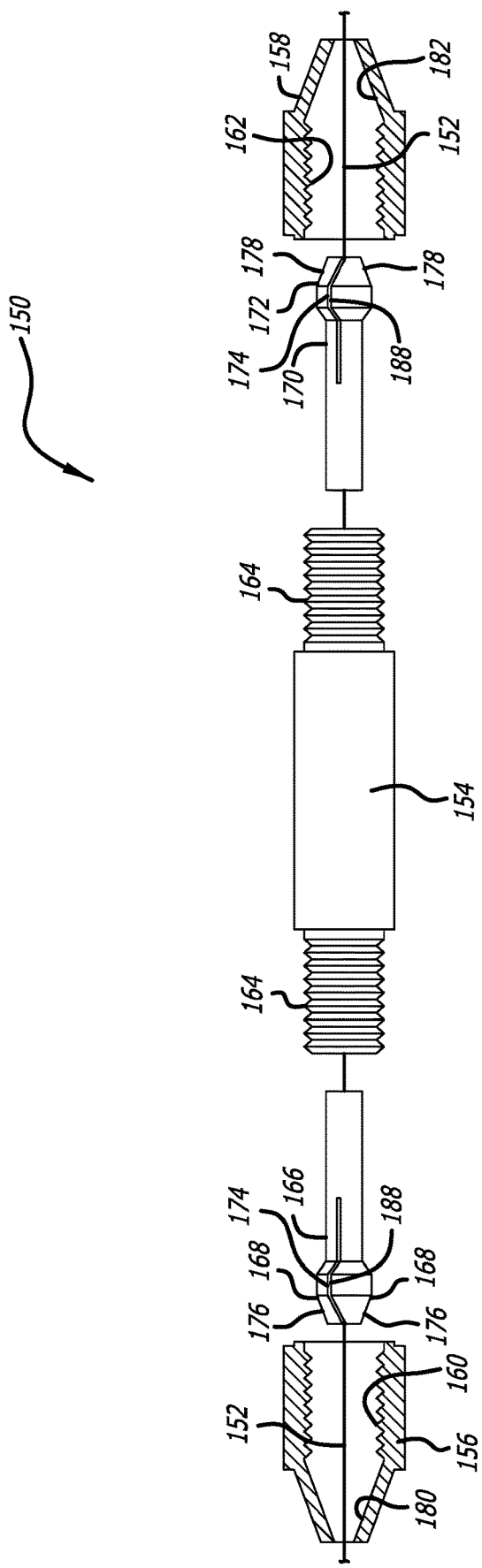
FIG. 17A is a side elevational, exploded view, of a torque device for use in gripping and manipulating a guidewire.
Figure 17B:
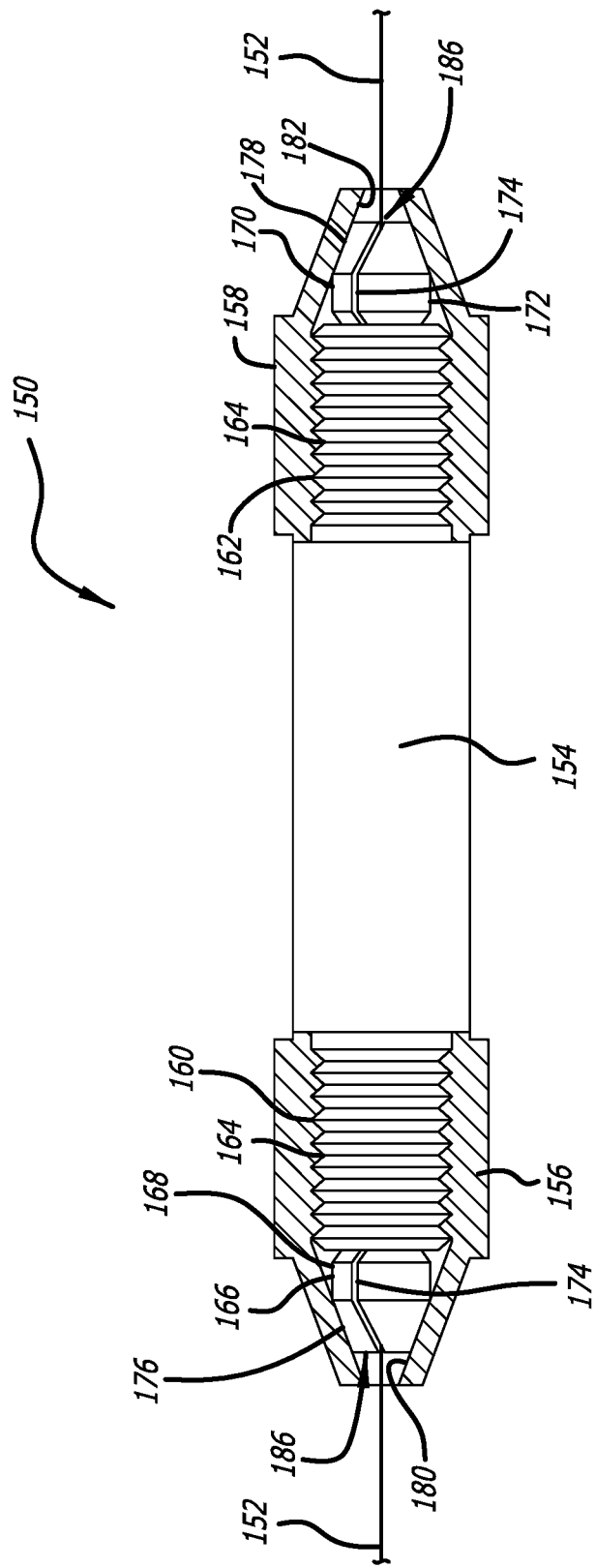
FIG. 17B is a side cross-sectional view of the torque device of FIG. 17A.
Figure 18:
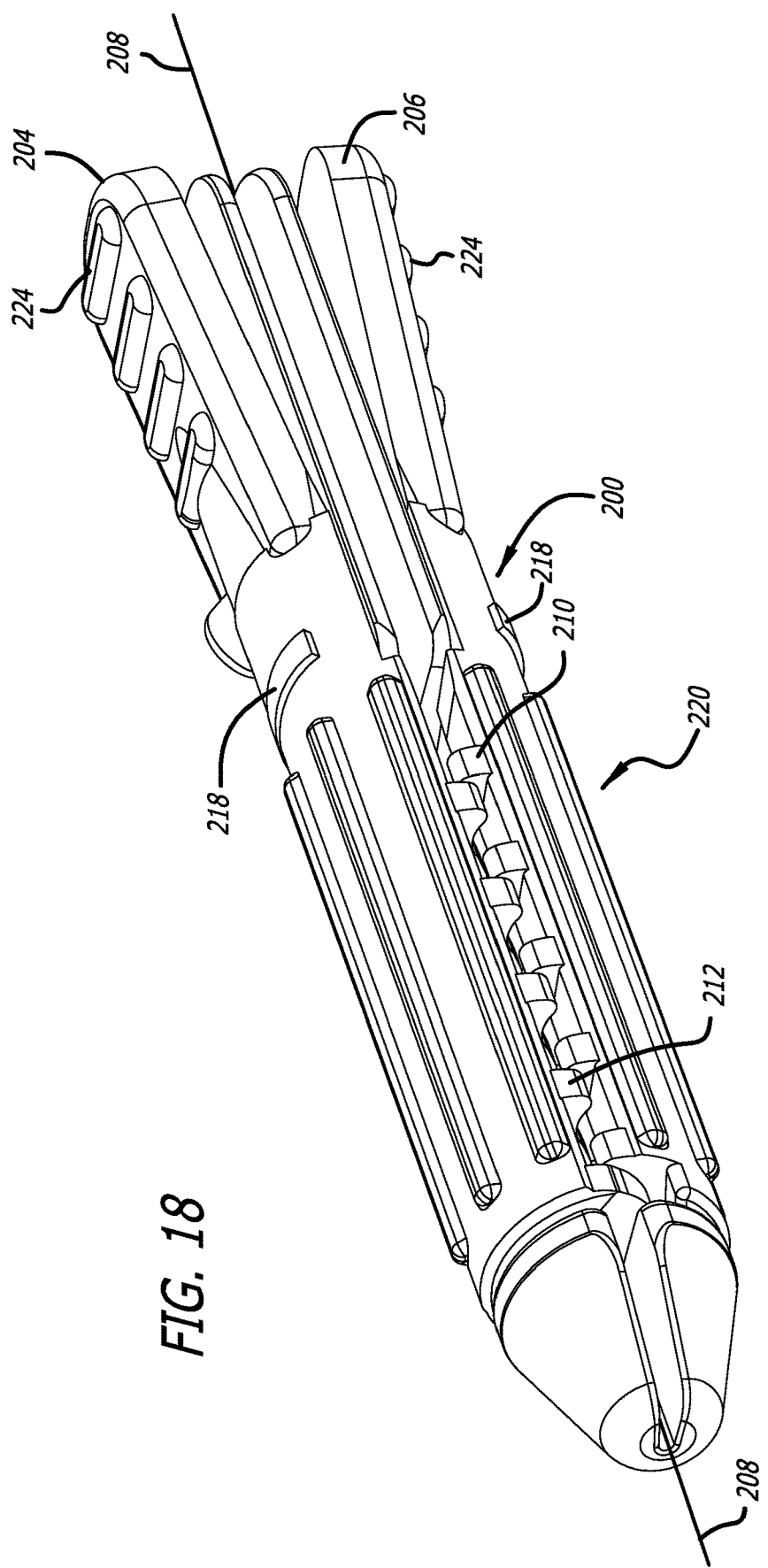
FIG. 18 is a perspective view of a torque device for use in gripping and manipulating a guidewire.

In another embodiment, as shown in FIGS. 17A and 17B, a torque device 150 is used to grip, manipulate and release a guidewire 152 using two hands to operate the device. Importantly, in this embodiment, the torque device applies gripping force on the guidewire at two separate locations, thereby doubling the gripping force which allows the physician to more easily manipulate and advance the guidewire. The torque device 150 includes a body 154 and a first cap 156 and a second cap 158. The body 154 has body threads 164 on each end and the first cap 156 has first threads 160 so that the first cap 156 can be screwed onto one end of the body. The second cap 158 has second threads 162 so that the second cap 158 can be screwed on the end of the body 154 opposite the first cap 156. A first collet 166 is connected or attached to a second collet 170, and both are attached to the body 154. The first collet 166 has first fingers 168 and the second collet 170 has second fingers 172, the first fingers 168 pointing in a direction opposite to that of the second fingers 172. The first collet 166 and the second collet 170 are enclosed in the body 154 and in the first cap 156 and the second cap 158 respectively when the caps are screwed onto the body 154. The first collet 166 and the second collet 170 float within the body 154. In order for the first collet 166 and the second collet 170 to apply gripping force on the guidewire 152, the first cap 156 and the second cap 158 are screwed onto the body 154 thereby enclosing the first collet 166 and the second collet 170 inside the caps. A tapered surface 176 on the first collet 166 slidably engages a tapered surface 180 on the first cap 156 thereby forcing the first fingers 168 towards a compressed position 186. Similarly, as the second cap 158 screws onto the body 154, a tapered surface 178 on the second collet 170 slidably engages a tapered surface 182 on the second cap 158 thereby compressing the second fingers 172 into the compressed position 186. Each of the first fingers 168 and the second fingers 172 has a gripping surface 174 that directly contacts the guidewire 152 when the fingers are in the compressed position 186. Importantly, the compressed position 186 between the first fingers 168 and the second fingers 172 are spaced apart thereby providing two points of contact or gripping force on the guidewire and doubling the gripping force (as compared to a single contact surface) without damaging the guidewire or any coating thereon. The first collet 166 and the second collet 170 are formed from any metal or polymer that will not damage the guidewire, and preferably are made from brass. By unscrewing the first cap 156 and the second cap 158 from the body 154, the first fingers 168 and the second fingers 172 will spring open to an open position 188 since the fingers are spring biased toward an open position. In other words, as the first cap 156 is unscrewed from the body 154, the tapered surface 176 of the first collet 166 slidingly moves away from the tapered surface 180 of the first cap, thereby allowing the first fingers 168 to spring radially outwardly away from each other since they are spring biased open. This moves the first fingers 168 toward the open position 188. Likewise, as the second cap 158 is unscrewed from the body 154, the tapered surface 178 on the second collet 170 slides away from the tapered surface 182 of the second cap 158 allowing the second fingers 172 to spring radially outwardly open toward the open position 188. In the open position 188, the torque device can be moved axially along the guidewire 152 so that it can be repositioned and then the first cap 156 and the second cap 158 again screwed onto the body 154 to again move both sets of fingers to the compressed position 186.

Figure 19:
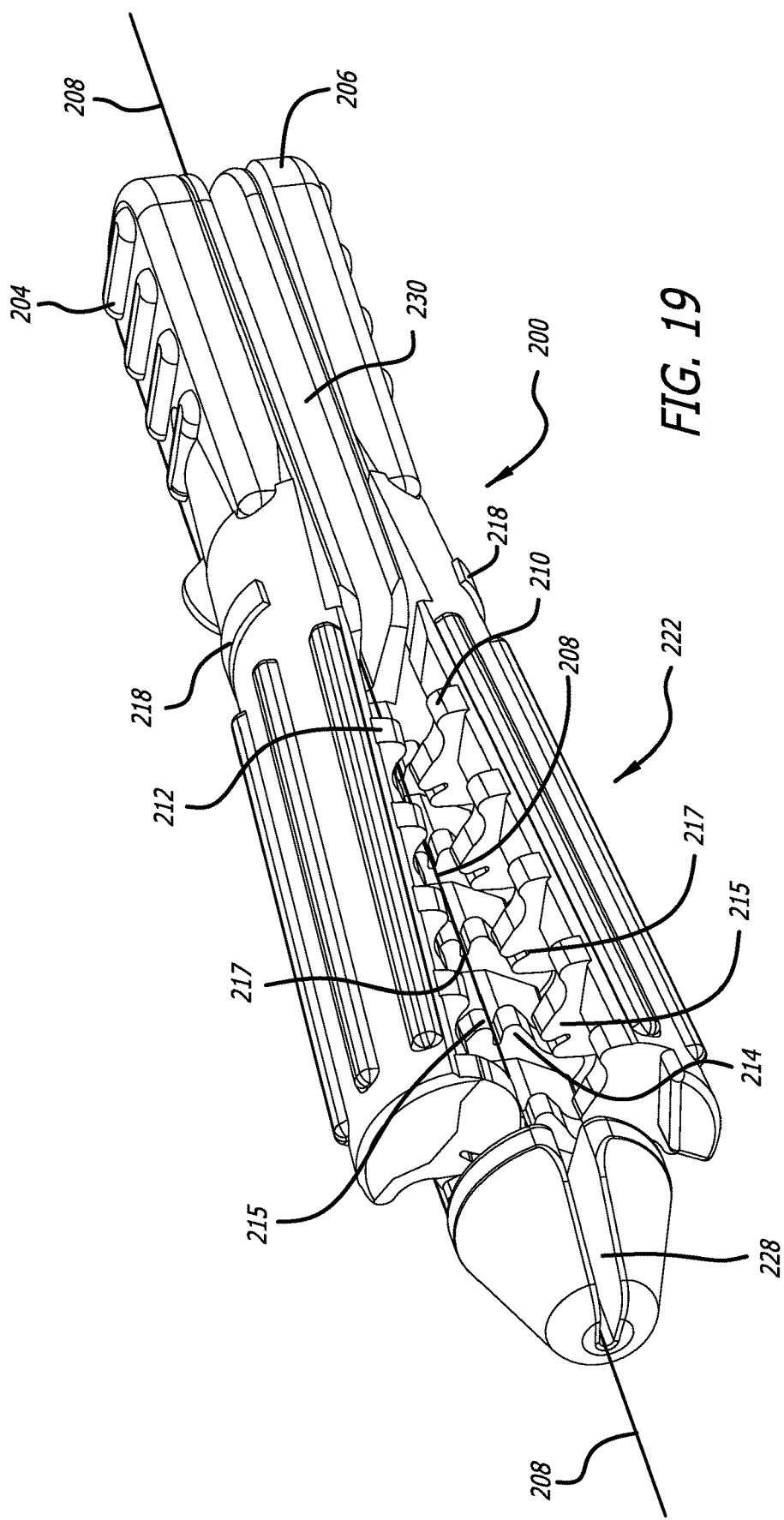
FIG. 19 is a perspective view of the torque device of FIG. 18.
Figure 20:
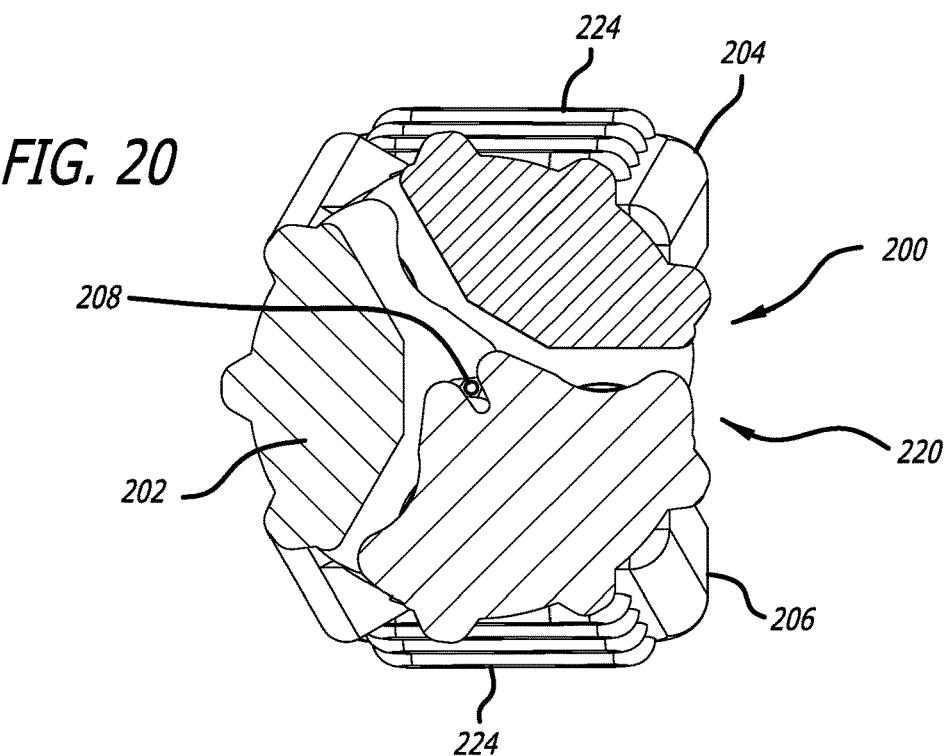
FIG. 20 is a distal end view of the torque device of FIG. 18.
Figure 21:
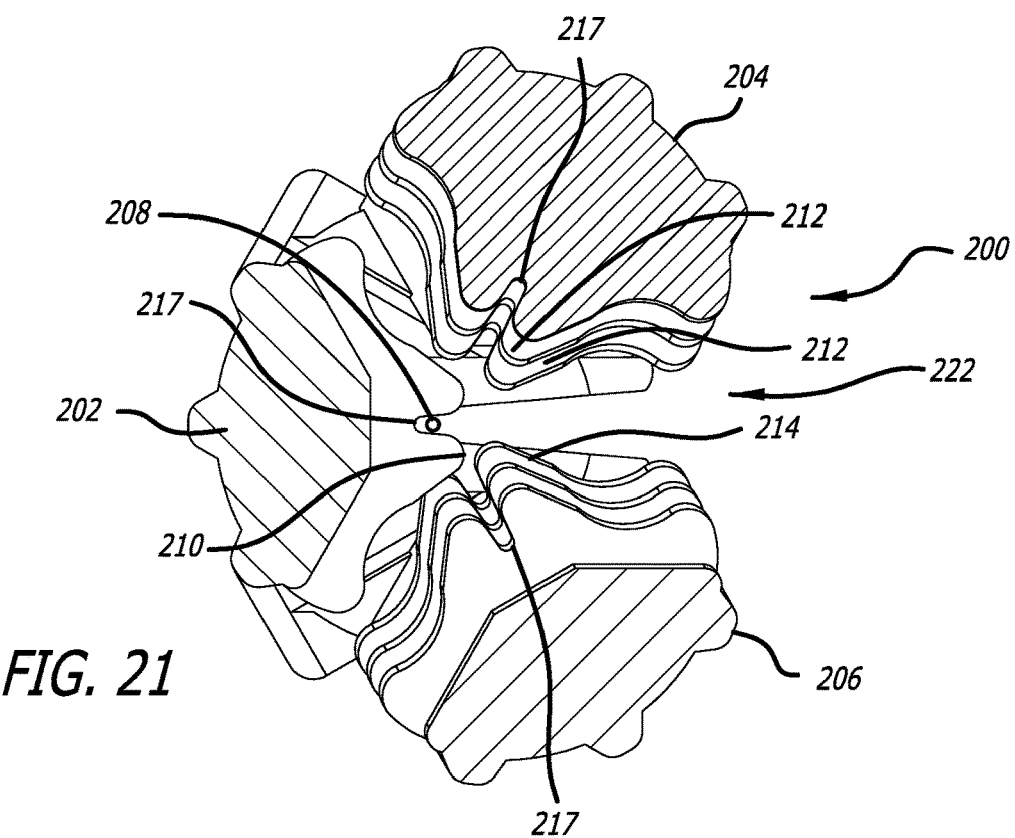
FIG. 21 is a distal end view of the torque device of FIG. 18.
Figure 22:
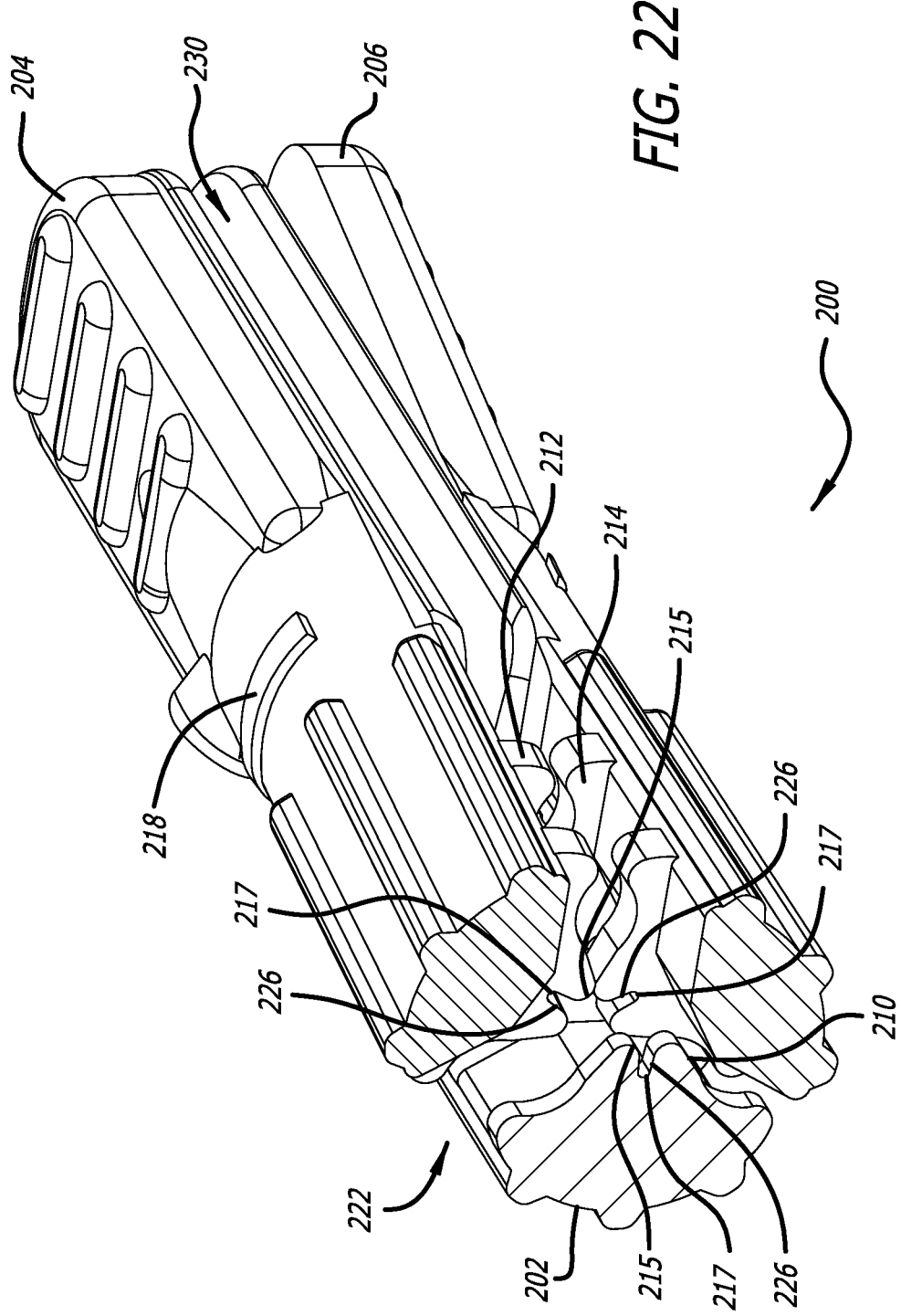
FIG. 22 is a perspective, partially exploded, view of the torque device of FIG. 18.
Figure 23:
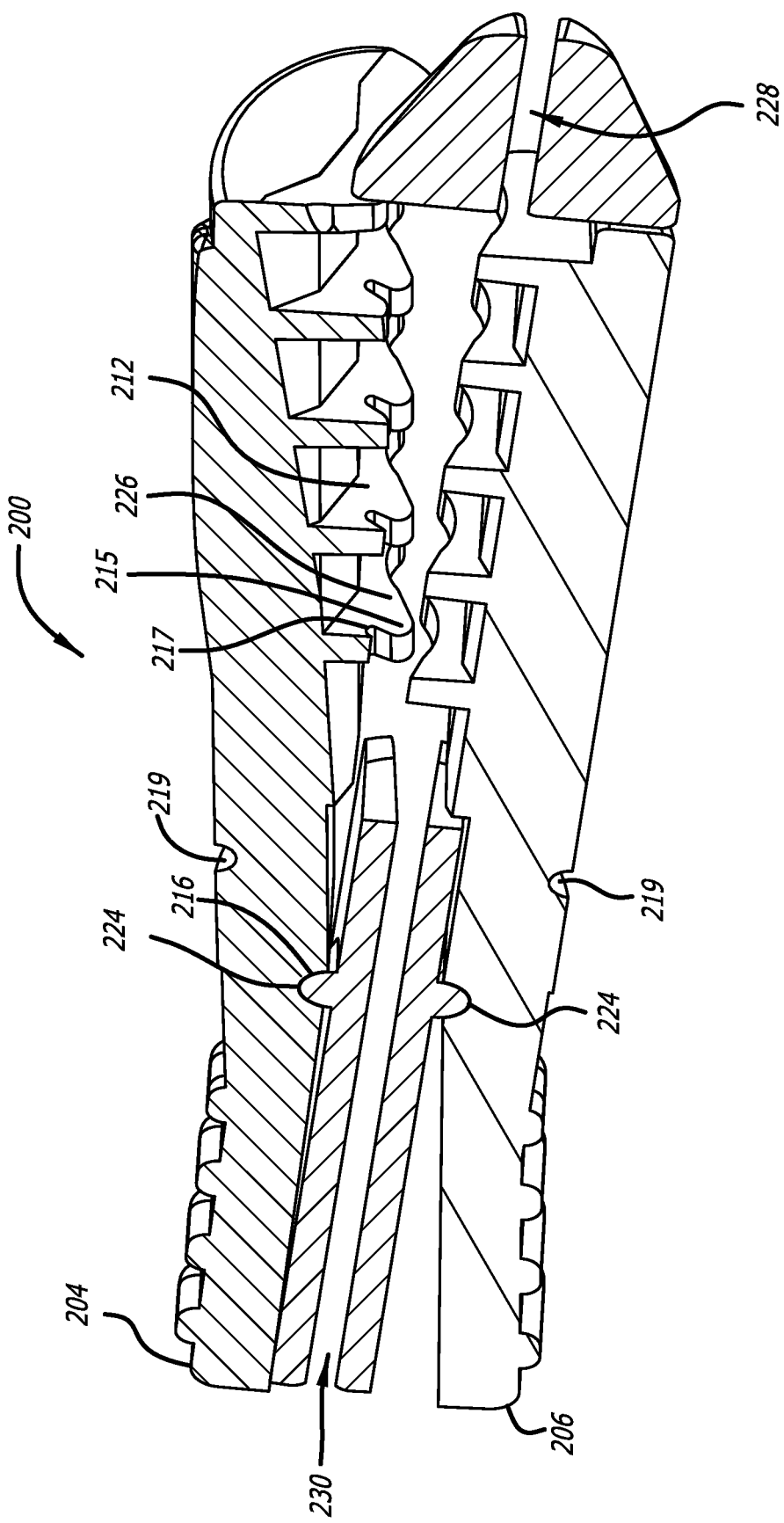
FIG. 23 is a side cross-sectional view of the torque device of FIG. 18.
Figure 24:
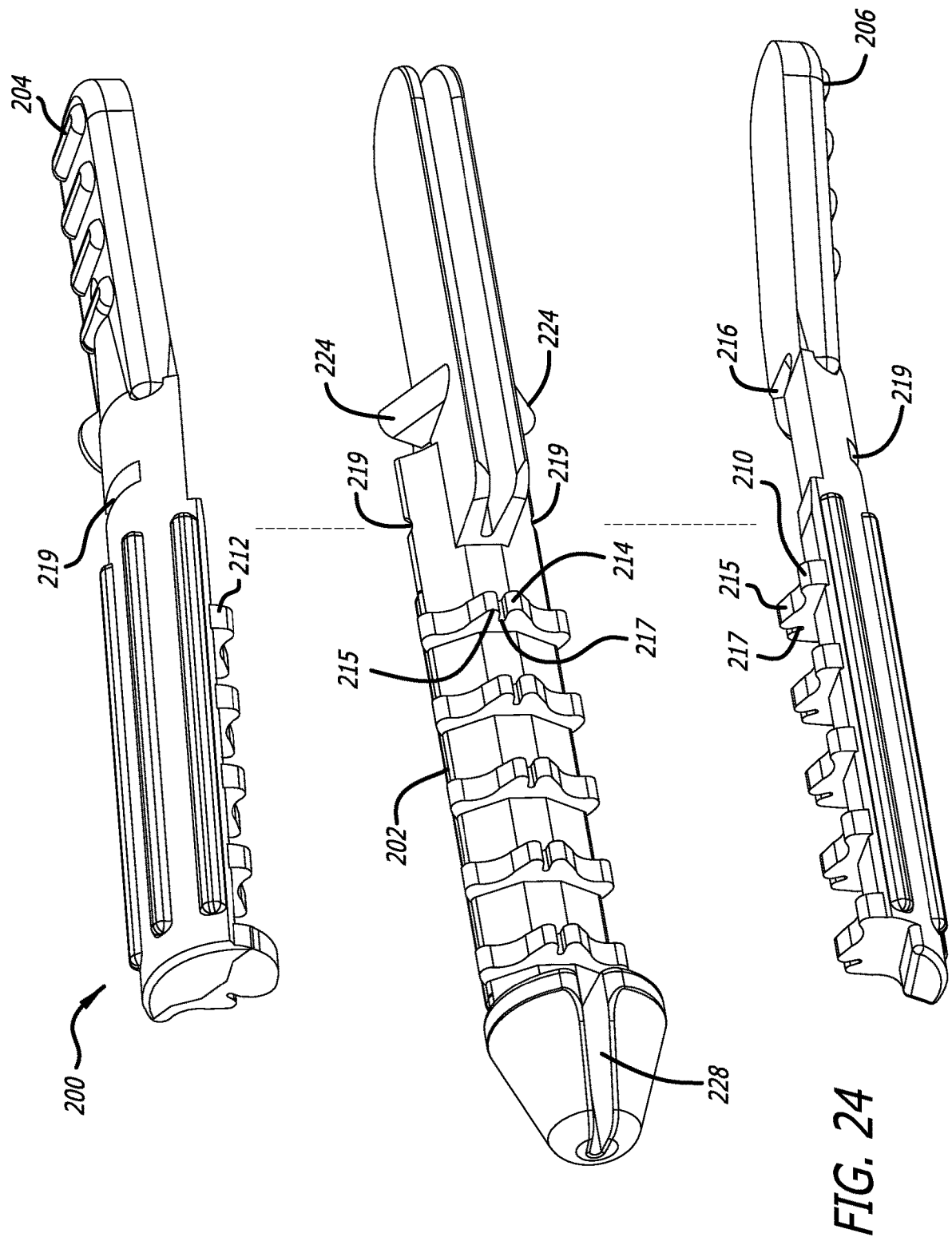
FIG. 24 is an exploded view of the three elements comprising the torque device of FIG. 18.

In another embodiment shown in FIGS. 18-24, three elements including a main element 202, a first element 204, and a second element 206, have V-shaped ribs that nest into one another. The V-shape is configured so that the guidewire 208 is side loaded and pushed into one set of the V's by the other V's. The main element 202 has main V-shaped ribs 214, the first element 204 has first V-shaped ribs 212, and the second element 206 has second V-shaped ribs 210. The guidewire clamping force is roughly the torquer grasping force geometrically multiplied by 1/sin of half of the angle of the V. A CAD model of the V-shaped ribs design has been generated with a preferred V-angle of 10 degrees. The V-angle can range from 0.5 degrees to 30 degrees. The V-angle also can range from 4 degrees to 15 degrees. The first element 204 and the second element 206 are connected to the main element by a hinge 216 in such a manner that their V geometry moves open and closed within approximately 120 degree planes. The pivoting motion of the first element 204 and the second element 206 also provides a means to open the two elements relative to the main element 202 and to one another. The three elements are removably connected to each other by a C-spring 218 that wraps partially around the elements and provides a spring bias force toward a closed position 220. The C-spring 218 fits in channel 219 so that it does not slide along the torque device 200. Each of the main, first, and second V-shaped ribs 214, 212, 210 can have a plurality of V-shaped ribs 215, and preferably have from two to eight ribs 215. In one embodiment, as shown in FIGS. 19 and 22, each of the main, first and second V-shaped ribs 214, 212, 210 has five V-shaped ribs 215. Each of the V-shaped ribs 215 has a gripping well 217 which is the V-shaped recess that receives the guidewire 208. The gripping well 217 is sized so that the guidewire does not bottom out (extend to the bottom) in the gripping well. Instead, the gripping well 217 has a V-shape or a U-shape to accept the guidewire 208 and lock onto the guidewire when the torque device 200 is in the closed position 220. When in the closed position 220, the physician can manipulate the torque device to advance the guidewire 208 into the vascular system without the guidewire moving axially or rotationally relative to the toque device.

In an open position 222 (see FIGS. 19, 21, 22), the main, first and second V-shaped ribs 214, 212, 210, open large enough so that the guidewire 208 may be side loaded between the first V-shaped ribs 212 and the second V-shaped ribs 210. When the V-shaped ribs are collapsed toward one another, the V-shaped geometries contact the guidewire. As long as at least two of the V-shaped ribs are compressed towards one another (the torque device being rolled between a users fingers), then the two V-shaped ribs which are being grasped apply force to be exerted on the guidewire from the associated V-shaped ribs. Thus, a user does not need to compress all three sets of V-shaped ribs at the same time, only two sets.

In use, the hinged main, first and second V-shaped ribs 214, 212, 210 have release tabs 224 that move into and out of recess 216. When the user compresses or lightly compresses any two of the main, first or second elements 202, 204, 206 toward each other, the release tabs 224 move about the recess 216 and cause the V-shaped ribs to start to open, releasing the guidewire 208. The V-shapes 226 of the V-shaped ribs may act like strippers and strip the guidewire from the opposing V-shapes. Since the V-shaped ribs 214, 212, 210 are held together with the C-spring 218, it allows for side loading the guidewire and a light preload on the V-shaped ribs to be spring biased toward the closed/grasping position, which provides frictional drag on the guidewire when not being handled. If the user wants to move the torque device 200 along the guidewire, the user lightly compresses the release tabs 224, thus slightly opening the V-shaped ribs so that the torque device can easily slide along the guidewire.

The main element 202 has a distal trough 228 and a proximal trough 230 to facilitate side loading and locating the guidewire 208 centrally within the main, first and second V-shaped ribs 214, 212, 210. The distal and proximal troughs 228, 230 on the main V-shaped rib 210 also provide structural access for over the wire guidewire embodiments.

Figure 27:
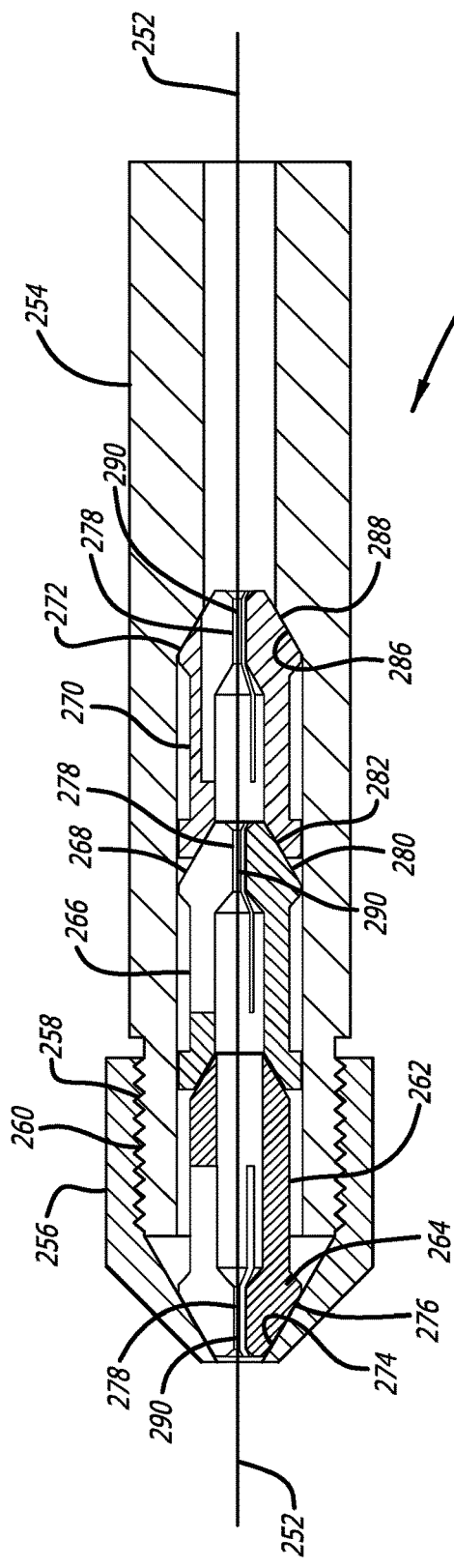
FIG. 27 is a side, cross-sectional view, of the torque device of FIG. 25.

In another embodiment, as shown in FIGS. 25-27, a torque device 250 is used to grip, manipulate and release a guidewire 252 using two hands to operate the device. Importantly, in this embodiment, the torque device applies gripping force on the guidewire at multiple separate locations, thereby increasing the gripping force which allows the physician to more easily manipulate and advance the guidewire. The torque device 250 includes a body 254 and a cap 256. The body 254 has body threads 258 and the cap 256 has cap threads 260 so that the cap can be screwed onto the body. A first collet 262 is partially inserted into a second collet 266. The first collet has first fingers 264 and the second collet 266 has second fingers 268, the first fingers 264 pointing in a direction opposite to that of the second fingers 268. A third collet 270 has third fingers 272 that point in the same direction as second fingers 268. The third collet 270 is configured to partially receive the second collet 266. The first collet 262, the second collet 266, and the third collet 270 are enclosed in the cap 256 and the body 254 when the cap is screwed onto the body. In order for the first collet 262, the second collet 266, and the third collet 270 to apply gripping force on the guidewire 252, the cap 256 is screwed on the body 254 thereby enclosing and axially compressing the first collet 262, the second collet 266, and the third collet 270 inside the cap and the body. A tapered surface 274 on the first collet 262 engages a tapered surface 276 on the cap thereby forcing the first fingers 264 towards a compressed position 278 and thereby grip the guidewire 252. Similarly, as the cap 256 continues to screw onto the body portion 254, a tapered surface 280 on the second collet 266 engages a tapered surface 282 on a distal end 284 of the third collet 270 thereby compressing the second fingers 268 into the compressed position 278 and thereby grip the guidewire 252.

Further, as the cap 256 is screwed onto the body 254, a tapered surface 286 on the third collet 270 engages a tapered surface 282 on the body 254 thereby compressing the third fingers 272 into the compressed position 278 and thereby grip the guidewire 252. Each of the first fingers 264, the second fingers 268, and the third fingers 272, has a gripping surface 290 that directly contacts the guidewire 252 when the fingers are in the compressed position 278. Importantly, the gripping surface 290 among the first fingers 264, the second fingers 268, and the third fingers 272 are spaced apart thereby providing three points of contact or gripping force on the guidewire, thereby tripling the gripping force without damaging the guidewire or any coating thereon. The first collet 262, the second collet 266, and the third collet 270 are formed from any metal or polymer that will not damage the guidewire, and preferably are made from brass. By unscrewing the cap from the body, the fingers will open to an open position 292 since the fingers are spring biased toward an open position. In other words, as cap 256 is unscrewed from the body 254, the tapered surface 274 of the first collet 262 moves away from the tapered surface 276 of the cap, thereby allowing the first fingers to spring outwardly away from each other since they are spring biased open. This moves the first fingers 264 toward the open position 292 and thereby releasing the guidewire 252. Likewise, as the cap 256 is unscrewed from the body 254, the tapered surface 280 on the second collet 266 slides away from the tapered surface 282 of the third collet 270 allowing the second fingers 268 to spring radially outwardly open toward the open position 292 and thereby releasing the guidewire 252.

As the cap 256 is further unscrewed from the body 254, the tapered surface 286 on the third collet 270 slides away from the tapered surface 288 on the body 254 allowing the third fingers 272 to spring radially outwardly open toward the open position 292 and thereby releasing the guidewire 252. In the open position 292, the torque device 250 can be moved axially along the guidewire 252 so that it can be repositioned and then the cap 256 again screwed onto the body 254 to move all the fingers to the compressed position 278.

Figure 28:
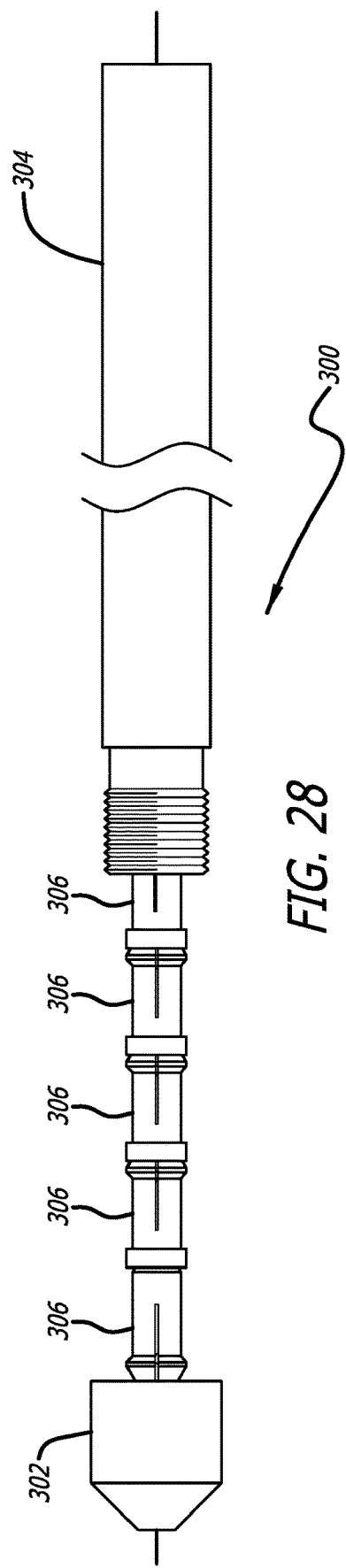
FIG. 28 is a side view of a torque device for use in gripping and manipulating a guidewire having five spaced apart gripping locations.

In another embodiment, as shown in FIG. 28, a torque device 300 has a cap 302, a body 304, and multiple collets 306 that are used in the same manner and configuration as shown in FIGS. 25-27. In this embodiment, at least five collets are axially aligned to dovetail into each other to provide five, spaced apart gripping surfaces on the fingers. Importantly, more than two collets, and up to seven collets, can be axially aligned to provide enhanced gripping force spaced along the guidewire so that the physician can more easily manipulate, torque, and advance the guidewire during a procedure. It is preferred that all of the collets be of the same size and shape in order to simplify manufacturing and assembly. The number of collets used in this embodiment is limited only by the length of the housing and the length of each collet.

Figure 29:
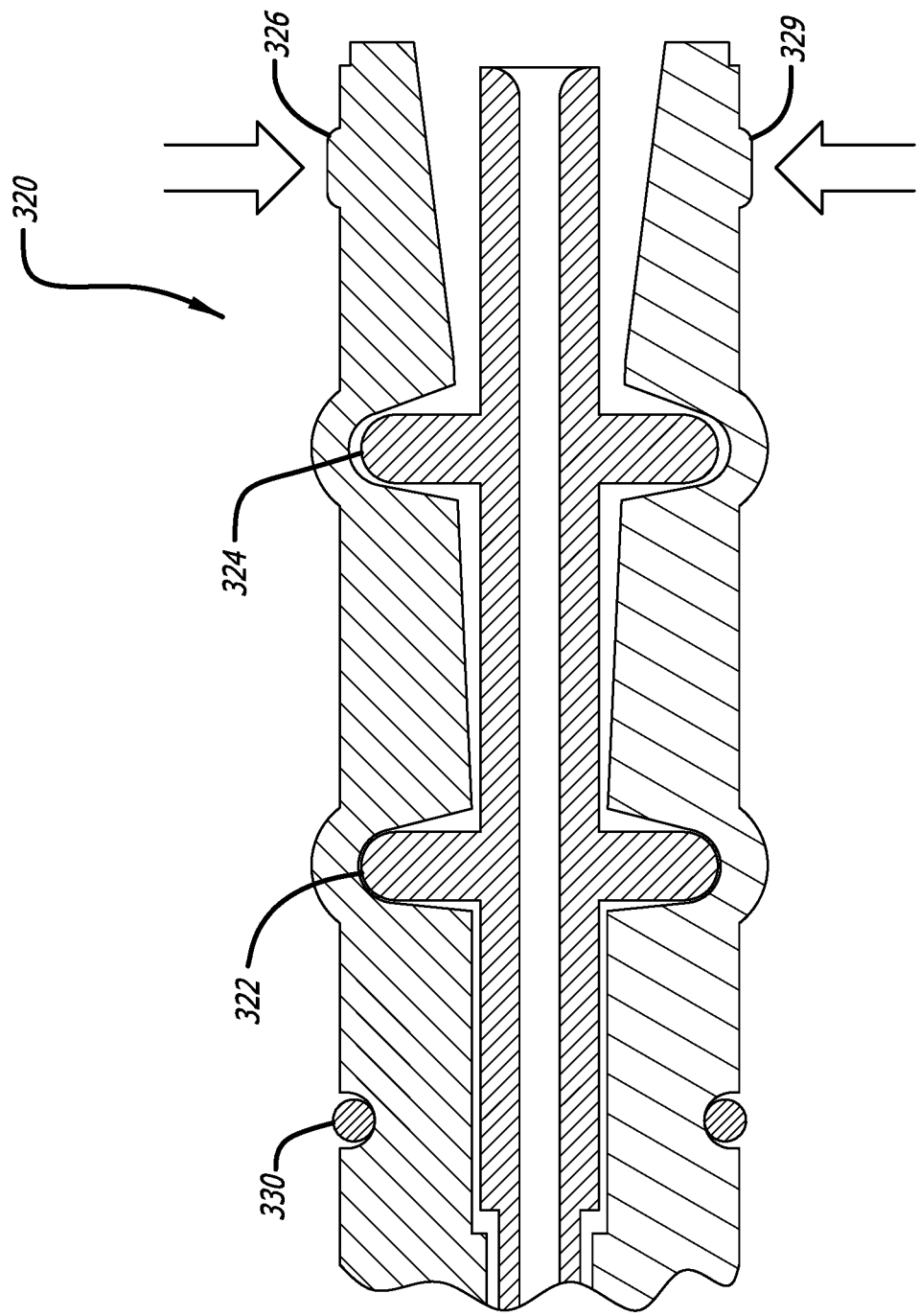
FIG. 29 is a partial elevational view of a torque device similar to the torque device depicted in FIGS. 18-24 with the differences being two hinges to open and close the device.

In another embodiment, shown in FIG. 29, a torque device 320 is identical in structure to the V-shaped ribs torque device shown in FIGS. 18-24, with one difference. In this embodiment, a first hinge 322 and a second hinge 324 provide a high degree of tactile feedback to the physician when gripping the guidewire and then opening the torque device 320 so it can be repositioned along the guidewire. In FIG. 29, the torque device is in the closed position and the V-shaped ribs are gripping the guidewire. To reposition the torque device 320, the user pinches a first element 326 and second element 328 at the arrows so that the first element 326 and the second element 328 pivot about first hinge 322 until the first and second elements contact the second hinge 324, which is about 1.5 degrees of travel. The first pivoting action provides tactile feedback to the user so that they may easily stop at the 1.5 degree opening to allow the torque device 320 be repositioned on or slide along the guidewire. If the user wants to remove the guidewire from the torque device (side access), a definite increase in compressive force by the user is required. Further compressing the first and second elements at the arrows results in an additional 5.0 degrees of rotation at second hinge 324. This results in the V-shaped ribs spreading apart and releasing the guidewire. A C-shaped spring 330 extends part way around the torque device 320 and is spring biased toward the closed position. When pressure by the user is removed from the first element 326 and the second element 328, the spring force of the C-shaped spring 330 closes the torque device 320. While the preferred amount of travel regarding the first hinge is 1.5 degrees and for the second hinge is 5.0 degrees, it is contemplated that any amount of travel in the range of 0.5 to 3.0 degrees for the first hinge 322, and 2.0 to 15.0 degrees for the second hinge 324, is advantageous.

It will be apparent from the foregoing that, while particular forms of the invention have been illustrated an described, various modifications can be made without departing from the spirit and scope of the invention. Moreover, those skilled in the art will recognize that features shown in one embodiment may be utilized in other embodiments.

We claim:

1. A device for gripping a guidewire, comprising:
   a body having a distal end, a proximal end and a substantially uniform opening therethrough;
   a collet having a plurality of fingers spring biased toward an open position;
   a cap for engaging the collet and compressing the fingers of the collet when the cap is tightened to the body portion, the cap configured to receive an end of a guidewire and including an opening through which a guidewire can pass;
   a tubular sleeve having a distal end, a proximal end, and a lumen extending therethrough for receiving the collet wherein the tubular sleeve has a tapered distal end configured for sliding engagement with a first tapered face of the collet as the tubular sleeve moves distally; and
   a control lever attached to the body and configured for moving the tubular sleeve into and out of engagement with the collet and moving the collet into and out of engagement with the cap thereby causing a gripping surface on the fingers to compress onto the guidewire and release from the guidewire.

2. The device of claim 1, wherein the body further comprises threads on the distal end, and the cap includes an opening having threads, the threads in the opening receiving the threads on the first end to tighten the cap to the body.

3. The device of claim 2 wherein the collet comprises multiple substantially parallel, longitudinally-extending fingers.

4. The device of claim 3, wherein the control lever is attached to the body by a pin so that the control lever can be actuated in an open and closed configuration.

5. The device of claim 4, wherein the control lever has a distal end and a proximal end, the distal end of the control lever having a cam.

6. The device of claim 5, wherein the cam on the distal end of the control lever engages a cam surface on the proximal end of the tubular sleeve.

7. The device of claim 6, wherein depressing the control lever to the closed position moves the cam into sliding engagement with the cam surface, thereby moving the tubular sleeve distally so that the distal end of the tubular sleeve engages the collet.

8. The device of claim 7, wherein the collet has a second tapered face.

9. The device of claim 8, wherein the tapered distal end of the tubular sleeve slides on the first tapered face of the collet and forces the collet to move distally.

10. The device of claim 9, wherein the second tapered face of the collet engages a tapered surface on the cap as the collet moves distally.

11. The device of claim 10, wherein the plurality of fingers compress onto the guidewire as the collet moves distally and the second tapered face of collet engages and slides along the tapered surface on the cap.

12. The device of claim 11, wherein a force vector is generated by the second tapered face of the collet sliding along the tapered surface of the cap, the force vector overcoming the spring bias of the plurality of fingers.

13. The device of claim 6, wherein depressing the control lever to the open position moves the cam into sliding disengagement with the cam surface.

14. The device of claim 13, wherein after the cam disengages from the cam surface, the plurality fingers being spring biased to the open position, spring apart to the open position thereby moving the collet and the tubular sleeve proximally to cause the gripping surface on the collet to release the guidewire.

15. The device of claim 14, wherein the second tapered surface of the collet slides proximally on the cap tapered surface thereby releasing the plurality of fingers to spring apart to the open position.

16. A method for gripping and maneuvering a guidewire, comprising:
    providing a torque device having a body, a collet having a plurality of fingers spring biased toward an open position, and a cap for engaging the collet;
    compressing the plurality of fingers of the collet by tightening the cap to the body portion, the cap configured to receive an end of a guidewire and including an opening through which a guidewire can pass;
    inserting a guidewire through the body, the collet, and the cap;
    wherein the collet has a first tapered face and a second tapered face, and wherein the tubular sleeve has a tapered distal end configured for sliding engagement with the first tapered face of the collet as the tubular sleeve moves distally, and as the tapered distal end of the tubular sleeve slides on the first tapered face of the collet the sleeve forces the collet to move distally; and
    depressing a control lever attached to the body and configured for moving a sleeve into and out of engagement with the collet and moving the collet into and out of engagement with the cap thereby causing a gripping surface on the fingers to compress onto the guidewire and release from the guidewire.

17. The method of claim 16, wherein the body further comprises threads on the distal end, and of the body threads on a proximal end of the cap, the threads on the cap receiving the threads on the distal end of the body to screw the cap onto the body thereby compressing the plurality of fingers on the collet.

18. The method of claim 17, wherein the control lever has a distal end and a proximal end, the distal end of the control lever having a cam, and by depressing the control lever to the closed position, the cam slides along a proximal end of the sleeve to move the sleeve and collet distally toward the cap.

19. The method of claim 18, wherein the cam on the distal end of the control lever slidingly engages a cam surface on the proximal end of the tubular sleeve.

20. The method of claim 19, wherein the second tapered face of the collet engages a tapered surface on the cap as the collet moves distally thereby compressing the plurality of fingers onto the guidewire as the collet moves distally and the second tapered face of collet engages and slides along the tapered surface on the cap.

21. The method of claim 20, wherein a force vector is generated by the second tapered face of the collet sliding along the tapered surface of the cap, the force vector overcoming the spring bias of the plurality of fingers.

22. The method of claim 16, wherein depressing the control lever to the open position moves the control lever cam into sliding disengagement with the sleeve cam surface.

23. The method of claim 22, wherein after the control lever cam disengages from the sleeve cam surface, the plurality of the fingers spring apart to the open position thereby moving the collet and the tubular sleeve proximally to cause the gripping surface on the collet to release the guidewire.

24. The method of claim 23, wherein the collet second tapered surface slides proximally on the cap tapered surface thereby releasing the plurality of fingers to spring apart to the open position and release the guidewire.

* * * * *